(12) United States Patent
Borg et al.

(10) Patent No.: US 8,722,043 B2
(45) Date of Patent: May 13, 2014

(54) INDUCTION OF P53 EXPRESSION BY NEUTRALIZATION OF NEUROPILIN-2 FOR THE TREATMENT OF CANCERS

(75) Inventors: Christophe Borg, Pouillet les Vignes (FR); John Wijdenes, Larnod (FR); Camille Grandclement, Besançon (FR)

(73) Assignees: Diaclone, Besancon (FR); EFS Bourgogne Franche Comte, Besancon (FR); Universite de Franche Comte, Besancon (FR)

( * ) Notice: Subject to any disclaimer, the term of this patent is extended or adjusted under 35 U.S.C. 154(b) by 299 days.

(21) Appl. No.: 13/060,889

(22) PCT Filed: Aug. 26, 2009

(86) PCT No.: PCT/FR2009/001035
§ 371 (c)(1),
(2), (4) Date: Oct. 18, 2011

(87) PCT Pub. No.: WO2010/023382
PCT Pub. Date: Mar. 4, 2010

(65) Prior Publication Data
US 2012/0027779 A1 Feb. 2, 2012

(30) Foreign Application Priority Data
Aug. 27, 2008 (FR) ..................... 08 04725

(51) Int. Cl.
*A61K 39/395* (2006.01)
*C07K 16/00* (2006.01)
(52) U.S. Cl.
USPC ................ 424/133.1; 424/155.1; 530/387.7

(58) Field of Classification Search
None
See application file for complete search history.

(56) References Cited

U.S. PATENT DOCUMENTS

2006/0251650 A1   11/2006   Klagsbrun et al.

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Sulpice, Neuropilin-1 and neuropilin-2 act as coreceptors, potentiating proangiogenic activity, Blood, 111, 2036-2045, (2008).
Caunt, Blocking Neuropilin-2 Function Inhibits Tumor Cell Metastasis, Cancer Cell 13, 331-342, (2008).
Favier, Neuropilin-2 interacts with VEGFR-2 and VEGFR-3 and promotes human endothelial cell survival and migration, Blood, 108, 1243-1250, (2006).
Gray, Therapeutic Targeting of Neuropilin-2 on Colorectal Carcinoma Cells Implanted in the Murine Liver, JNCI 2008, 100, 109-120, (2008).
Futamura, Possible Role of Semaphorin 3F, a Candidate Tumor Suppressor Gene at 3p21.3, in p53-Regulated Tumor Angiogenesis Suppression, American Association for Cancer Research, 67, 1451-1460, (2007).

* cited by examiner

*Primary Examiner* — Sheela J Huff
(74) *Attorney, Agent, or Firm* — Morgan, Lewis & Bockius LLP

(57) ABSTRACT

The present invention relates to the use of anti-human neuropilin-2 antibodies, or of ligands of human neuropilin-2 derived from these antibodies, for obtaining a medicament intended to increase p53 expression and to induce tumor cell apoptosis in the context of an anticancer treatment.

9 Claims, 16 Drawing Sheets

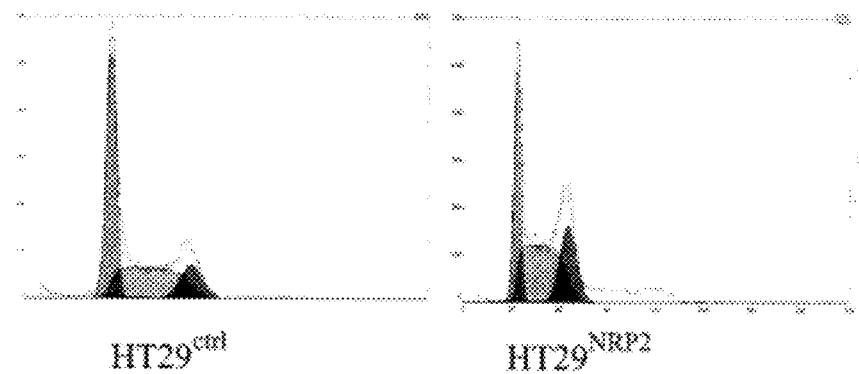
Figure 4 bis

SEQUENCE LISTING

```
<160> NUMBER OF SEQ ID NOS: 32

<210> SEQ ID NO 1
<211> LENGTH: 349
<212> TYPE: DNA
<213> ORGANISM: Mus musculus
<220> FEATURE:
<221> NAME/KEY: CDS
<222> LOCATION: (1)..(348)
<220> FEATURE:
<221> NAME/KEY: V_region
<222> LOCATION: (1)..(294)
<220> FEATURE:
<221> NAME/KEY: misc_feature
<222> LOCATION: (1)..(75)
<223> OTHER INFORMATION: FR1
<220> FEATURE:
<221> NAME/KEY: misc_feature
<222> LOCATION: (76)..(99)
<223> OTHER INFORMATION: CDR1
<220> FEATURE:
<221> NAME/KEY: misc_feature
<222> LOCATION: (100)..(150)
<223> OTHER INFORMATION: FR2
<220> FEATURE:
<221> NAME/KEY: misc_feature
<222> LOCATION: (151)..(174)
<223> OTHER INFORMATION: CDR2
<220> FEATURE:
<221> NAME/KEY: misc_feature
<222> LOCATION: (175)..(288)
<223> OTHER INFORMATION: FR3
<220> FEATURE:
<221> NAME/KEY: misc_feature
<222> LOCATION: (286)..(318)
<223> OTHER INFORMATION: JUNCTION
<220> FEATURE:
<221> NAME/KEY: misc_feature
<222> LOCATION: (289)..(315)
<223> OTHER INFORMATION: CDR3
<220> FEATURE:
<221> NAME/KEY: misc_feature
<222> LOCATION: (316)..(349)
<223> OTHER INFORMATION: FR4

<400> SEQUENCE: 1 gaa gtt aag ctg cag gag tca ggg gca gag ctt gtg aag cca ggg gcc        48
```

```
                Glu Val Lys Leu Gln Glu Ser Gly Ala Glu Leu Val Lys Pro Gly Ala
                1               5                   10                  15 tca gtc aag ttg tcc tgc aca gtt tct ggc ttc aac att aaa gac acc        96
Ser Val Lys Leu Ser Cys Thr Val Ser Gly Phe Asn Ile Lys Asp Thr
            20                  25                  30 tat ata cac tgg gtg ata cag agg cct gaa cag ggc ctg gag tgg ctt       144
Tyr Ile His Trp Val Ile Gln Arg Pro Glu Gln Gly Leu Glu Trp Leu
            35                  40                  45 gga agg att gat cct gcg aat ggt aat act aaa tat gac ccg aag ttc       192
Gly Arg Ile Asp Pro Ala Asn Gly Asn Thr Lys Tyr Asp Pro Lys Phe
    50                  55                  60 cag ggc aag gcc act ata aca gca gac aca tcc tcc aac aca gcc tac       240
Gln Gly Lys Ala Thr Ile Thr Ala Asp Thr Ser Ser Asn Thr Ala Tyr
65                  70                  75                  80 ctg cag ctc agc agc ctg acc tct gag gac act gcc gtc tat tac tgt       288
Leu Gln Leu Ser Ser Leu Thr Ser Glu Asp Thr Ala Val Tyr Tyr Cys
                85                  90                  95 gct aga tgg gcg gtt gta ggt gac tac tgg ggc caa ggc acc act ctc       336
Ala Arg Trp Ala Val Val Gly Asp Tyr Trp Gly Gln Gly Thr Thr Leu
                100                 105                 110 aca gtc tcc tca g                                                     349
Thr Val Ser Ser
        115

<210> SEQ ID NO 2
<211> LENGTH: 116
<212> TYPE: PRT
<213> ORGANISM: Mus musculus

<400> SEQUENCE: 2

Glu Val Lys Leu Gln Glu Ser Gly Ala Glu Leu Val Lys Pro Gly Ala
1               5                   10                  15

Ser Val Lys Leu Ser Cys Thr Val Ser Gly Phe Asn Ile Lys Asp Thr
            20                  25                  30

Tyr Ile His Trp Val Ile Gln Arg Pro Glu Gln Gly Leu Glu Trp Leu
            35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Trp Ala Val Val Gly Asp Tyr Trp Gly Gln Gly Thr Thr Leu
                100                 105                 110

Thr Val Ser Ser
        115

<210> SEQ ID NO 3
<211> LENGTH: 318
<212> TYPE: DNA
<213> ORGANISM: Mus musculus
<220> FEATURE:
<221> NAME/KEY: V_region
<222> LOCATION: (1)..(283)
<220> FEATURE:
<221> NAME/KEY: misc_feature
<222> LOCATION: (1)..(77)
<223> OTHER INFORMATION: FR1
<220> FEATURE:
<221> NAME/KEY: CDS
<222> LOCATION: (3)..(317)
<220> FEATURE:
<221> NAME/KEY: misc_feature
```

```
<222> LOCATION: (78)..(95)
<223> OTHER INFORMATION: CDR1
<220> FEATURE:
<221> NAME/KEY: misc_feature
<222> LOCATION: (96)..(146)
<223> OTHER INFORMATION: FR2
<220> FEATURE:
<221> NAME/KEY: misc_feature
<222> LOCATION: (147)..(155)
<223> OTHER INFORMATION: CDR2
<220> FEATURE:
<221> NAME/KEY: misc_feature
<222> LOCATION: (156)..(263)
<223> OTHER INFORMATION: FR3
<220> FEATURE:
<221> NAME/KEY: misc_feature
<222> LOCATION: (261)..(290)
<223> OTHER INFORMATION: JUNCTION
<220> FEATURE:
<221> NAME/KEY: misc_feature
<222> LOCATION: (264)..(287)
<223> OTHER INFORMATION: CDR3
<220> FEATURE:
<221> NAME/KEY: misc_feature
<222> LOCATION: (288)..(318)
<223> OTHER INFORMATION: FR4

<400> SEQUENCE: 3 ga tat tgt gat cac cca ctc tac aaa ttc ctg cat gta tca gca gga      47
   Tyr Cys Asp His Pro Leu Tyr Lys Phe Leu His Val Ser Ala Gly
    1               5                  10                  15 gac agg gtt acc ata acc tgc aag gcc agt cag agt gtg agt gat gat     95
Asp Arg Val Thr Ile Thr Cys Lys Ala Ser Gln Ser Val Ser Asp Asp
                 20                  25                  30 gtg gct tgg tac caa cag aag cca ggg cag tct cct aaa ctg ctg ata    143
Val Ala Trp Tyr Gln Gln Lys Pro Gly Gln Ser Pro Lys Leu Leu Ile
             35                  40                  45 tac tct gca tcc aat cgc tac act gga gtc cct gat cgc ttc act ggc    191
Tyr Ser Ala Ser Asn Arg Tyr Thr Gly Val Pro Asp Arg Phe Thr Gly
         50                  55                  60 agt gga tat ggg acg gat ttc act ttc acc atc agc act gtg cag cct    239
Ser Gly Tyr Gly Thr Asp Phe Thr Phe Thr Ile Ser Thr Val Gln Pro
     65                  70                  75 gaa gac ctg gca gtt tat ttc tgt cag cag gat tat agc tct ccc acg    287
Glu Asp Leu Ala Val Tyr Phe Cys Gln Gln Asp Tyr Ser Ser Pro Thr
 80                  85                  90                  95 ttc ggt tct ggg acc aag ctg gag ctg aaa c                          318
Phe Gly Ser Gly Thr Lys Leu Glu Leu Lys
                100                 105

<210> SEQ ID NO 4
<211> LENGTH: 105
<212> TYPE: PRT
<213> ORGANISM: Mus musculus

<400> SEQUENCE: 4

Tyr Cys Asp His Pro Leu Tyr Lys Phe Leu His Val Ser Ala Gly Asp
 1               5                  10                  15

Arg Val Thr Ile Thr Cys Lys Ala Ser Gln Ser Val Ser Asp Asp Val
             20                  25                  30

Ala Trp Tyr Gln Gln Lys Pro Gly Gln Ser Pro Lys Leu Leu Ile Tyr
         35                  40                  45

Ser Ala Ser Asn Arg Tyr Thr Gly Val Pro Asp Arg Phe Thr Gly Ser
     50                  55                  60

Gly Tyr Gly Thr Asp Phe Thr Phe Thr Ile Ser Thr Val Gln Pro Glu
 65                  70                  75                  80
```

Asp Leu Ala Val Tyr Phe Cys Gln Gln Asp Tyr Ser Ser Pro Thr Phe
            85                  90                  95

Gly Ser Gly Thr Lys Leu Glu Leu Lys
            100                 105

<210> SEQ ID NO 5
<211> LENGTH: 358
<212> TYPE: DNA
<213> ORGANISM: Mus musculus
<220> FEATURE:
<221> NAME/KEY: CDS
<222> LOCATION: (1)..(357)
<220> FEATURE:
<221> NAME/KEY: V_region
<222> LOCATION: (1)..(295)
<220> FEATURE:
<221> NAME/KEY: misc_feature
<222> LOCATION: (1)..(75)
<223> OTHER INFORMATION: FR1
<220> FEATURE:
<221> NAME/KEY: misc_feature
<222> LOCATION: (76)..(99)
<223> OTHER INFORMATION: CDR1
<220> FEATURE:
<221> NAME/KEY: misc_feature
<222> LOCATION: (100)..(150)
<223> OTHER INFORMATION: FR2
<220> FEATURE:
<221> NAME/KEY: misc_feature
<222> LOCATION: (151)..(174)
<223> OTHER INFORMATION: CDR2
<220> FEATURE:
<221> NAME/KEY: misc_feature
<222> LOCATION: (175)..(288)
<223> OTHER INFORMATION: FR3
<220> FEATURE:
<221> NAME/KEY: misc_feature
<222> LOCATION: (286)..(327)
<223> OTHER INFORMATION: JUNCTION
<220> FEATURE:
<221> NAME/KEY: misc_feature
<222> LOCATION: (289)..(324)
<223> OTHER INFORMATION: CDR3
<220> FEATURE:
<221> NAME/KEY: misc_feature
<222> LOCATION: (325)..(358)
<223> OTHER INFORMATION: FR4

<400> SEQUENCE: 5 gag gtg cag ctg gag gag tca ggg gga ggc tta gtg aag cct gga ggg      48
Glu Val Gln Leu Glu Glu Ser Gly Gly Gly Leu Val Lys Pro Gly Gly
1               5                   10                  15 tcc ctg aaa ctc tcc tgt gca gcc tct gga ttc act ttc agt gac tat      96
Ser Leu Lys Leu Ser Cys Ala Ala Ser Gly Phe Thr Phe Ser Asp Tyr
            20                  25                  30 tac atg tat tgg gtt cgc cag act ccg gaa aag agg ctg gag tgg gtc     144
Tyr Met Tyr Trp Val Arg Gln Thr Pro Glu Lys Arg Leu Glu Trp Val
        35                  40                  45 gca acc att agt gat ggt ggt agt tac acc tac tat cca gac agt att     192
Ala Thr Ile Ser Asp Gly Gly Ser Tyr Thr Tyr Tyr Pro Asp Ser Ile
    50                  55                  60 aag ggc cga ttc acc atc tcc agg gac aat gcc agg aac aac ctg tac     240
Lys Gly Arg Phe Thr Ile Ser Arg Asp Asn Ala Arg Asn Asn Leu Tyr
65                  70                  75                  80 ctt caa atg agc agt ctg aag tct gag gac aca gcc atg tat tac tgt     288
Leu Gln Met Ser Ser Leu Lys Ser Glu Asp Thr Ala Met Tyr Tyr Cys
                85                  90                  95 gca aga ggt ggg ccc tat agg tcc tgg ttt gct ttc tgg ggc caa ggg     336
Ala Arg Gly Gly Pro Tyr Arg Ser Trp Phe Ala Phe Trp Gly Gln Gly
            100                 105                 110

```
act ctg gtc act gtc tct gca g                                    358
Thr Leu Val Thr Val Ser Ala
        115

<210> SEQ ID NO 6
<211> LENGTH: 119
<212> TYPE: PRT
<213> ORGANISM: Mus musculus

<400> SEQUENCE: 6

Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Tyr Thr Tyr Tyr Pro Asp Ser Ile
    50                  55                  60

Lys Gly Arg Phe Thr Ile Ser Arg Asp Asn Ala Arg Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Gly Gly Pro Tyr Arg Ser Trp Phe Ala Phe Trp Gly Gln Gly
            100                 105                 110

Thr Leu Val Thr Val Ser Ala
        115

<210> SEQ ID NO 7
<211> LENGTH: 337
<212> TYPE: DNA
<213> ORGANISM: Mus musculus
<220> FEATURE:
<221> NAME/KEY: CDS
<222> LOCATION: (1)..(336)
<220> FEATURE:
<221> NAME/KEY: V_region
<222> LOCATION: (1)..(302)
<220> FEATURE:
<221> NAME/KEY: misc_feature
<222> LOCATION: (1)..(78)
<223> OTHER INFORMATION: FR1
<220> FEATURE:
<221> NAME/KEY: misc_feature
<222> LOCATION: (79)..(111)
<223> OTHER INFORMATION: CDR1
<220> FEATURE:
<221> NAME/KEY: misc_feature
<222> LOCATION: (112)..(162)
<223> OTHER INFORMATION: FR2
<220> FEATURE:
<221> NAME/KEY: misc_feature
<222> LOCATION: (163)..(171)
<223> OTHER INFORMATION: CDR2
<220> FEATURE:
<221> NAME/KEY: misc_feature
<222> LOCATION: (172)..(279)
<223> OTHER INFORMATION: FR3
<220> FEATURE:
<221> NAME/KEY: misc_feature
<222> LOCATION: (277)..(309)
<223> OTHER INFORMATION: JUNCTION
<220> FEATURE:
<221> NAME/KEY: misc_feature
<222> LOCATION: (280)..(306)
<223> OTHER INFORMATION: CDR3
<220> FEATURE:
<221> NAME/KEY: misc_feature
<222> LOCATION: (307)..(337)
<223> OTHER INFORMATION: FR4
```

```
<400> SEQUENCE: 7 gat att gtg atc acc cag act cca ctc tcc ctg cct gtc agt ctt gga    48
Asp Ile Val Ile Thr Gln Thr Pro Leu Ser Leu Pro Val Ser Leu Gly
1               5                   10                  15 gat caa gcc tcc atc tct tgc aga tct agt cag agc att gtg tat agt    96
Asp Gln Ala Ser Ile Ser Cys Arg Ser Ser Gln Ser Ile Val Tyr Ser
            20                  25                  30 aat gga aac acc tat tta gaa tgg tac ctg cag aaa cca ggc cag tct    144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca    192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc    240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt    288
Ser Arg Val Glu Ala Glu Asp Leu Gly Val Tyr Tyr Cys Phe Gln Gly
                85                  90                  95 tca cat gtt cct ccg acg ttc ggt gga ggc acc aag ctg gaa atc aaa c  337
Ser His Val Pro Pro Thr Phe Gly Gly Gly Thr Lys Leu Glu Ile Lys
            100                 105                 110

<210> SEQ ID NO 8
<211> LENGTH: 112
<212> TYPE: PRT
<213> ORGANISM: Mus musculus

<400> SEQUENCE: 8

Asp Ile Val Ile Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 9
<211> LENGTH: 8
<212> TYPE: PRT
<213> ORGANISM: Mus musculus

<400> SEQUENCE: 9

Gly Phe Asn Ile Lys Asp Thr Tyr
1               5

<210> SEQ ID NO 10
<211> LENGTH: 8
<212> TYPE: PRT
<213> ORGANISM: Mus musculus

<400> SEQUENCE: 10

Ile Asp Pro Ala Asn Gly Asn Thr
1               5
```

<210> SEQ ID NO 11
<211> LENGTH: 9
<212> TYPE: PRT
<213> ORGANISM: Mus musculus

<400> SEQUENCE: 11

Ala Arg Trp Ala Val Val Gly Asp Tyr
1               5

<210> SEQ ID NO 12
<211> LENGTH: 6
<212> TYPE: PRT
<213> ORGANISM: Mus musculus

<400> SEQUENCE: 12

Gln Ser Val Ser Asp Asp
1               5

<210> SEQ ID NO 13
<211> LENGTH: 3
<212> TYPE: PRT
<213> ORGANISM: Mus musculus

<400> SEQUENCE: 13

Ser Ala Ser
1

<210> SEQ ID NO 14
<211> LENGTH: 8
<212> TYPE: PRT
<213> ORGANISM: Mus musculus

<400> SEQUENCE: 14

Gln Gln Asp Tyr Ser Ser Pro Thr
1               5

<210> SEQ ID NO 15
<211> LENGTH: 8
<212> TYPE: PRT
<213> ORGANISM: Mus musculus

<400> SEQUENCE: 15

Gly Phe Thr Phe Ser Asp Tyr Tyr
1               5

<210> SEQ ID NO 16
<211> LENGTH: 8
<212> TYPE: PRT
<213> ORGANISM: Mus musculus

<400> SEQUENCE: 16

Ile Ser Asp Gly Gly Ser Tyr Thr
1               5

<210> SEQ ID NO 17
<211> LENGTH: 12
<212> TYPE: PRT
<213> ORGANISM: Mus musculus

<400> SEQUENCE: 17

Ala Arg Gly Gly Pro Tyr Arg Ser Trp Phe Ala Phe
1               5                   10

<210> SEQ ID NO 18

-continued

```
<211> LENGTH: 11
<212> TYPE: PRT
<213> ORGANISM: Mus musculus

<400> SEQUENCE: 18

Gln Ser Ile Val Tyr Ser Asn Gly Asn Thr Tyr
1               5                   10

<210> SEQ ID NO 19
<211> LENGTH: 3
<212> TYPE: PRT
<213> ORGANISM: Mus musculus

<400> SEQUENCE: 19

Lys Val Ser
1

<210> SEQ ID NO 20
<211> LENGTH: 9
<212> TYPE: PRT
<213> ORGANISM: Mus musculus

<400> SEQUENCE: 20

Phe Gln Gly Ser His Val Pro Pro Thr
1               5

<210> SEQ ID NO 21
<211> LENGTH: 23
<212> TYPE: DNA
<213> ORGANISM: Artificial Sequence
<220> FEATURE:
<223> OTHER INFORMATION: Synthetic PCR PRIMER

<400> SEQUENCE: 21
gargttaagc tgsaggagtc agg                                          23

<210> SEQ ID NO 22
<211> LENGTH: 27
<212> TYPE: DNA
<213> ORGANISM: Artificial Sequence
<220> FEATURE:
<223> OTHER INFORMATION: Synthetic PCR PRIMER

<400> SEQUENCE: 22
atagacagat gggggtgtcg ttttggc                                      27

<210> SEQ ID NO 23
<211> LENGTH: 23
<212> TYPE: DNA
<213> ORGANISM: Artificial Sequence
<220> FEATURE:
<223> OTHER INFORMATION: Synthetic PCR PRIMER

<400> SEQUENCE: 23
gaggtgcagc tggaggagtc agg                                          23

<210> SEQ ID NO 24
<211> LENGTH: 27
<212> TYPE: DNA
<213> ORGANISM: Artificial Sequence
<220> FEATURE:
<223> OTHER INFORMATION: Synthetic PCR PRIMER

<400> SEQUENCE: 24
atagacagat gggggtgtcg ttttggc                                      27
```

-continued

```
<210> SEQ ID NO 25
<211> LENGTH: 24
<212> TYPE: DNA
<213> ORGANISM: Artificial Sequence
<220> FEATURE:
<223> OTHER INFORMATION: Synthetic PCR PRIMER

<400> SEQUENCE: 25
gatattgtga tsacmcardc taca                                              24

<210> SEQ ID NO 26
<211> LENGTH: 22
<212> TYPE: DNA
<213> ORGANISM: Artificial Sequence
<220> FEATURE:
<223> OTHER INFORMATION: Synthetic PCR PRIMER

<400> SEQUENCE: 26
ggatacagtt ggtgcagcat ta                                                22

<210> SEQ ID NO 27
<211> LENGTH: 24
<212> TYPE: DNA
<213> ORGANISM: Artificial Sequence
<220> FEATURE:
<223> OTHER INFORMATION: Synthetic PCR PRIMER

<400> SEQUENCE: 27
gatattgtgm tsacccagac tcca                                              24

<210> SEQ ID NO 28
<211> LENGTH: 22
<212> TYPE: DNA
<213> ORGANISM: Artificial Sequence
<220> FEATURE:
<223> OTHER INFORMATION: Synthetic PCR PRIMER

<400> SEQUENCE: 28
ggatacagtt ggtgcagcat ta                                                22

<210> SEQ ID NO 29
<211> LENGTH: 23
<212> TYPE: DNA
<213> ORGANISM: Homo sapiens

<400> SEQUENCE: 29
aaaggctgga agtcagcact aat                                               23

<210> SEQ ID NO 30
<211> LENGTH: 23
<212> TYPE: DNA
<213> ORGANISM: Homo sapiens

<400> SEQUENCE: 30
aaaaattagt gctgacttcc agc                                               23

<210> SEQ ID NO 31
<211> LENGTH: 22
<212> TYPE: RNA
<213> ORGANISM: Artificial
<220> FEATURE:
<223> OTHER INFORMATION: Synthetic siRNA

<400> SEQUENCE: 31
ggcuggaagu cagcacuaau uu                                                22
```

```
<210> SEQ ID NO 32
<211> LENGTH: 22
<212> TYPE: RNA
<213> ORGANISM: Artificial
<220> FEATURE:
<223> OTHER INFORMATION: Synthetic siRNA

<400> SEQUENCE: 32
auuagugcug acuuccagcc uu                                            22
```

INDUCTION OF P53 EXPRESSION BY NEUTRALIZATION OF NEUROPILIN-2 FOR THE TREATMENT OF CANCERS

RELATED APPLICATIONS

The present application is a U.S. National Phase Application of International Application No. PCT/FR2009/001035 (filed Aug. 26, 2009), which claims priority to French Patent No. 0804725 (filed Aug. 27, 2008) which are hereby incorporated by reference in their entirety.

Sequence Listing Submission Via EFS-Web

A computer readable text file, entitled "045636-5164_SequenceListing.txt," created on or about Feb. 24, 2011, with a file size of about 18 kb contains the sequence listing for this application and is hereby incorporated by reference in its entirety.

The present invention relates to the treatment of cancer by overexpression of the p53 tumour suppressor gene and induction of tumour cell apoptosis by targeting of neuropilin-2.

Cancer is characterized by an uncontrolled cell proliferation generally due to mutations in the genes that upregulate (oncogenes) or downregulate (tumour suppressor genes) cell proliferation. By virtue of their anarchical proliferation, tumour cells locally invade healthy tissue and, after having undergone further mutations, may acquire the ability to migrate in the blood stream and to propagate remotely from the initial tumour so as to form metastases. However, neovascularization of the tumour by the angiogenesis mechanism is essential to tumour growth since any cell, and in particular tumour cells which have a very high oxygen and energy demand, cannot survive at more than a few ten millimeters or so from a blood vessel.

The current anticancer treatments therefore have as their main targets, on the one hand, the tumour cells themselves and, on the other hand, the tumour angiogenesis.

As regards the anti-angiogenesis strategies, the involvement of growth factors, in particular EGF or VEGF (Vascular Endothelial Growth Factor), in the progression of cancers and in angiogenesis has been demonstrated. Several molecules that target the action of VEGFs have been developed as anti-angiogenesis medicaments: a bevacizumab (Avastin®), which is to humanized monoclonal antibody directed against VEGF, has been used since 2004 for the treatment of metastatic colorectal cancer; sunitinib and sorafenib, which are molecules that inhibit signal transduction in the VEGF/VEGF-receptor pathway, have been used in anti-angiogenesis strategies for the treatment of metastatic renal carcinoma.

As regards the strategies targeting the tumour and the tumour cells, surgical ablation of tumour tissues (when this is possible), solid-tumour radiotherapy, immunotherapies aiming at strengthening the immune responses against the cancer cells, and chemotherapies represent the standard therapeutic treatments. The major advances in the understanding of the molecular mechanisms of cancerogenesis have made it possible to develop new chemotherapies, the effectiveness of which depends, however, on the type of cancer to be treated and on the organ affected. In addition, many cancers also pose major public health problems and prove to be resistant to conventional therapies. For example, gastrointestinal cancers (pancreatic cancer, cholangiocarcinomas, colorectal cancers) rapidly become resistant to chemotherapy over the course of their natural history. Loss of the tumour suppressor gene encoding the p53 protein is one of the major mechanisms that explains the resistance of tumour cells to apoptosis and to conventional anti-neoplastic treatments such as chemotherapy or radiotherapy. This is because the function of the p53 protein is to arrest the cell cycle or to induce apoptosis of a cell in response to damage to the cellular DNA or to oncogene activation. The p53 protein therefore plays a central role in the control of the cell cycle and in maintaining the integrity of the genome, by allowing the cell whose cell cycle is interrupted to repair the genetic anomaly, or else by bringing about its destruction through apoptosis. Since p53 is essential for protecting the organism against the effects of aberrant or uncontrolled cell division, the absence of p53, its underexpression or the expression of a nonfunctional p53 protein results in the survival of tumour cells.

In an in vitro study model and in murine models, it has been shown that restoring p53 expression by gene transfer promotes cancer regression and improves the effectiveness of cytotoxic treatments. In vitro studies have also shown that, in cells expressing a wild-type protein and a mutant p53 protein having a dominant negative effect with respect to the wild-type protein, interference with an siRNA specifically targeting the mRNA encoding the mutant p53 protein re-establishes the function of p53 (Martinez et al. P.N.A.S., 99(23):14849-54, 2002). It has, moreover, been shown that it is possible to "reactivate" mutant p53 proteins by stabilizing a functional conformation of these proteins. The CP-31398, PRIMA-1 and MIRA-1 molecules, the first molecules developed that have this capacity, have been successfully used to inhibit tumour growth in a model of human xenograft (for review, cf. for example Levesque & Eastman, Carcinogenesis., 28(1): 13-20, 2007).

Restoration of the expression of a functional p53 protein, and also induction of the overexpression of this protein, therefore represent essential objectives in the development of anti-tumour therapies.

The inventors have now demonstrated the existence of an inverse correlation between neuropilin-2 (NRP-2) and expression of the p53 protein, and have shown that, surprisingly, p53 expression can be induced or increased by inhibiting neuropilin-2 expression using siRNA.

Neuropilin-2, a transmembrane glycoprotein of approximately 130 kDa, is a receptor for semaphorins, in particular semaphorin 3F, and for growth factors of the VEGF family. It is expressed in humans by neurons, endothelial cells and osteoblasts and by a wide variety of neoplasms. It is composed of an intracytoplasmic domain of approximately 40 amino acids, of a transmembrane domain and of an extracellular domain. This extracellular domain comprises a domain A, made up of 2 subdomains (a1a2), a domain B also made up of 2 subdomains (b1b2), and a domain C. It has been shown that the B domain constitutes the VEGF of binding site, whereas the binding with semaphorin 3F involved both the A domain and the B domain (Geretti et al., J. Biol. Chem., 282, 25698-707, 2007); the C domain is, for its part, involved in the oligomerization of NRP-2.

In many cases, the neuropilins are the only VEGF receptors expressed by cancer cells (Bielenberg et al. Exp. Cell. Res., 312(5):584-593, 2006), and several studies have shown that the expression, or even the overexpression, of neuropilins is generally correlated with an increase in tumour growth and in the invasive and metastatic nature of cancers, and also with an unfavourable prognosis.

In addition, many observations indicate that these receptors play an essential role in tumour progression by activating angiogenesis: in particular, the binding of VEGF to NRP-2 is responsible for a pro-angiogenic activity, mediated by cooperation between the short intracytoplasmic domain of NRP-2 and that of the VEGF receptor VEGFR1. It has been reported that NRP-2 has the ability to induce phosphorylation of the VEGFR1 receptor and of the AKT protein, thus favouring the progression of cancers, and that the suppression of neuropilin-2 with siRNA opposes the appearance of metastases in xenografts and reduces tumour size (Gray et al. J. Natl. Cancer Inst., 100:109-120, 2008). It has, moreover, been shown that an anti-NRP-2 antibody (called anti-Nrp2$^B$), directed against the VEGF-binding site of the B domain of NRP-2, can reduce tumour lymphangiogenesis and the formation of metastases; this antibody acts by inhibiting lymphatic endothelial cell migration, but has no effect on tumour cell migration, proliferation or apoptosis (Caunt et al., Cancer Cell, 13, 331-42, 2008).

The inventors have generated anti-NRP-2 antibodies and have noted that some of them produce the same effects on p53 expression and the induction of apoptosis of tumour cells as the inhibition of NRP-2 with siRNA, and that these effects are VEGF-independent. In addition, they have noted in vitro and in vivo in a murine model that these antibodies potentiate the effectiveness of anticancer treatments.

These data open up new therapeutic perspectives, in particular with regard to the possibility of developing innovative strategies for sensitization to chemotherapy or to radiotherapy or to other anticancer agents.

Thus, a subject of the present invention is an anti-human neuropilin-2 antibody, or a ligand of human neuropilin-2 derived from said antibody, characterized in that the binding thereof to tumour cells expressing human neuropilin-2 induces apoptosis of said tumour cells.

Advantageously, anti-human neuropilin-2 antibodies or ligands in accordance with the invention, in addition to their ability to induce apoptosis of tumour cells expressing human neuropilin-2, have the following characteristics:
  they induce p53 expression, and their ability to induce apoptosis is dependent on this p53 expression (it is decreased by a p53 inhibitor, pifithrin-α);
  their neuropilin-binding properties and their ability to induce apoptosis are VEGF-independent (their binding to the surface of tumour cells expressing human neuropilin-2 and their ability to induce apoptosis of said cells are not modified by the presence of VEGF).

Antibodies in accordance with the invention may thus be selected, from anti-human neuropilin-2 antibodies or from ligands derived therefrom, on the basis of their ability to induce apoptosis of tumour cells expressing human neuropilin-2, and/or on the basis of one or more of the other characteristics mentioned above.

The antibodies in accordance with the invention may be natural polyclonal or monoclonal antibodies, or recombinant antibodies, in particular chimeric or humanized antibodies. The term "chimeric antibody" is intended to mean an antibody which has the variable domains of the monoclonal antibody from which it is derived, coupled to the constant domains of another antibody, preferably a human antibody.

The term "humanized antibody" refers to an antibody initially produced by a nonhuman animal, preferably the mouse, having conserved its neuropilin-2-binding specificity, but in which, in order to reduce its immunogenicity in humans, as many murine sequences as possible have been replaced with the corresponding human sequences. As regards the variable domains, the sequences replaced are in general the FR (framework) regions, i.e. the sequences located between the hypervariable loops, CDRs.

Chimeric or humanized antibodies in accordance with the invention are preferably immunoglobulins of the IgG class, and in particular of isotypes IgG1, 2, 3 or 4.

The expression "ligand of human neuropilin-2 derived from an anti-neuropilin-2 antibody" is intended to mean any neuropilin-2 ligand comprising at least the CDR3s of the heavy chain and those of the light chain of said antibody, and preferably also comprising the CDR2s and/or the CDR1s of the heavy chain and of the light chain of said antibody.

Neuropilin-2 ligands in accordance with the invention may in particular be:
  any fragment of an anti-neuropilin-2 antibody in accordance with the invention comprising at least the CDR3s, and preferably also comprising the CDR2s and/or the CDR1s, of the heavy and light chains of said antibody;
  any recombinant protein, including a recombinant immunoglobulin molecule, comprising an anti-neuropilin-2 antibody fragment in accordance with the invention as defined above.

Anti-neuropilin-2 antibody fragments in accordance with the invention are in particular Fv, dsFv, Fab, Fab'2 or scFv fragments. The Fv fragments are constituted of the variable domains of the heavy and light chains, VH and VL, of an antibody, combined with one another via hydrophobic interactions. The dsFv fragment is constituted of a VH:: VL dimer linked via a disulphide bridge. The scFv fragments are constituted of the variable portions of the heavy and light chains of an antibody, linked to one another by means of a flexible linker (Clackson et al., Nature, 352: 624-628, 1991), thus forming a single-chain protein. The Fab fragments result from the action of papain on an immunoglobulin molecule, and each contain a light chain and the first half of a heavy chain, connected to one another by a disulphide bridge. The F(ab')2 fragment can be obtained by treatment of an antibody with pepsin: this fragment comprises two Fab fragments and a part of the hinge region. The Fab' fragments can be obtained from the F(ab')2 fragments by cleavage of the disulphide bridge in the hinge region.

These antigen-binding fragments may also be combined in order to obtain plurivalent derivatives, such as "diabodies" or "triabodies", resulting from the association of 2 or 3 of these antigen-binding fragments.

Recombinant proteins comprising an anti-neuropilin-2 antibody fragment in accordance with the invention may in particular be:
  proteins associating at least one anti-neuropilin-2 antibody fragment in accordance with the invention with at least one fragment of another antibody; by way of examples, mention will be made of bispecific immunoglobulins, conjugates of an Fv or Fab fragment of an anti-neuropilin-2 antibody with an Fv or Fab fragment of an antibody with a different specificity, "bispecific diabodies" resulting from the association of an scFv fragment of an anti-neuropilin-2 fragment with an Fv or Fab fragment of an antibody with a different specificity;
  proteins associating at least one anti-neuropilin-2 fragment in accordance with the invention with a molecule for prolonging its plasma half-life when it is administered in vivo, in particular with a water-soluble polypeptide of molecular mass sufficient for the molecular mass of the fusion polypeptide thus obtained to be greater than the renal filtration threshold.

BRIEF DESCRIPTION OF THE DRAWINGS

FIG. 4 bis illustrates the result of using an EPIC'C Altra cytometer and Wincycles cycle analysis software and shows that when cells express NRP-2, the number of cells in G2M and S phase increases, whereas the number of cells in G1 decreases.

Figure 1:
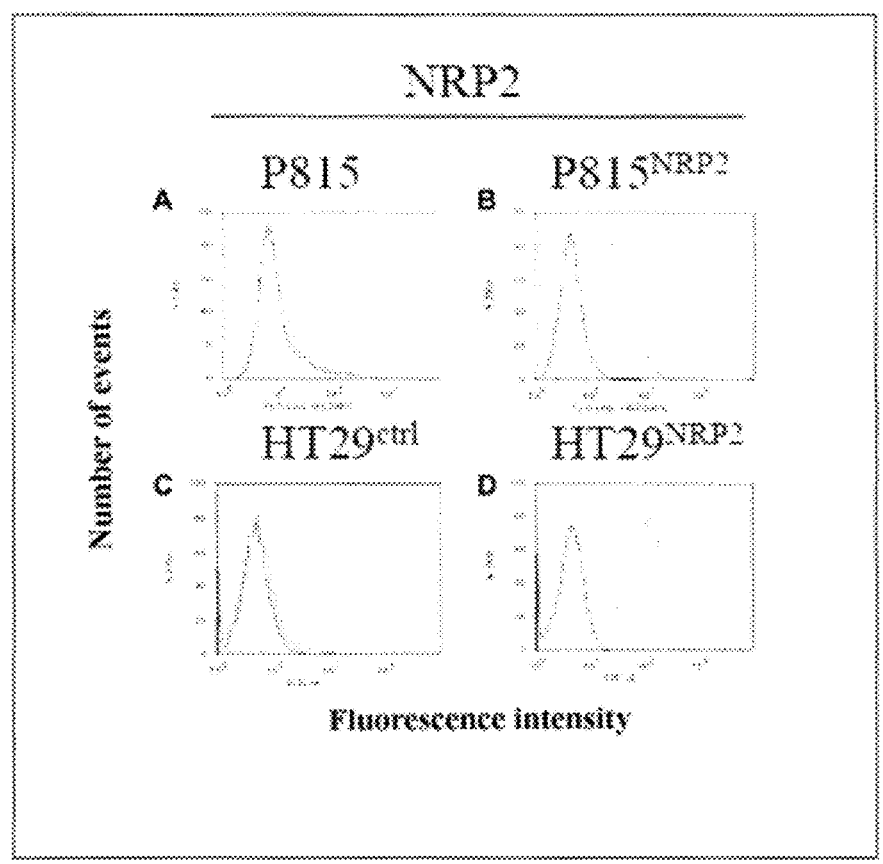
FIG. 1 illustrates the result of a flow cytometry study where panels A and C represent the results obtained by flow cytometry with control cells while panels B and D represent the results obtained with cells expressing NRP-2 at their membrane surface.

Chimeric or recombinant antibodies, scFv fragments and derivatives thereof, etc., can be obtained by conventional genetic engineering techniques, such as those described by Sambrook et al. (Molecular Cloning, A Laboratory Manual, 2nd Ed., Cold Spring Harbor Laboratory Press, Cold Spring Harbor, N.Y., 1989).

Polynucleotides encoding the variable regions of an anti-neuropilin-2 antibody in accordance with the invention can be obtained by cloning said regions from a library of cDNA of a hybridoma producing said antibodies. They can also be prepared completely or partially by nucleic acid synthesis, based on the nucleotide sequences of said variable regions.

Various methods for obtaining humanized antibodies are also well known in themselves (for review, cf., for example, Almagro & Fransson, Frontiers in Bioscience, 13, 1619-1633, 2008).

Mention may be made of the methods based on CDR grafting, which consists in transferring the CDRs of a non-human antibody into the framework regions (FR) of an antibody of human origin (cf., for example, Routledge et al., "Reshaping antibodies for therapy", in Protein Engineering of Antibody Molecules for Prophylatic and Therapeutic Applications in Man, 13-44, Academic Titles, Nottingham, England, 1993, or Roguska et al., Protein Engineering, 9(10): 895-904, 1996). The CDR grafting is generally completed by optimization of the framework regions, which consists in modifying some residues of the framework regions in order to increase the antigen-binding affinity of the humanized antibody. The use of combinatorial libraries makes it possible to simplify this optimization step (Rosok et al. J. Biol. Chem. 271: 22611-22618, 1996; Baca et al. J. Biol. Chem. 272: 10678-10684, 1997). Another strategy for antibody humanization consists in conserving only the CDR3s of the heavy and light chains of the antibody of origin, and in selecting the rest of the sequence from naive libraries of human V genes (Rader et al., *Proc. Natl. Acad. Sci. U.S.A.* 95: 8910-8915, 1998).

Two examples of anti-human neuropilin-2 monoclonal antibodies in accordance with the invention are the antibodies ITAC-B1 and ITAC-B2 described below. These monoclonal antibodies have been selected by the inventors on the basis of their ability to induce apoptosis of tumour cells expressing NRP-2.

The sequences of the heavy chain and of the light chain of ITAC-B1 and of ITAC-B2 were determined. These sequences, and also the deduced polypeptide sequences, are represented in Table 1 below (for the light chain and the heavy chain of ITAC-B1) and in Table 2 below (for the light chain and the heavy chain of ITAC-B2). The nucleotide sequences are also represented in the sequence listing in the annex, respectively under the numbers SEQ ID No. 1, 3, 5 and 7, and the polypeptide sequences are also represented, respectively, under the numbers SEQ ID No. 2, 4, 6 and 8.

The CNCM I-4054 hybridoma, which produces the ITAC-B1 antibody, was furthermore deposited, according to the Treaty of Budapest, on 30 Jul. 2008, with the Collection Nationale de Culture de Microorganismes [French National Microorganism Culture Collection] (Institut Pasteur, 25 rue du Docteur Roux, 75724 Paris Cedex 15, France, under the number CNCM I-4054.

TABLE 1

| ITAC-B1 |
| --- |
| Heavy chain (V-D-J region) |

| | |
| --- | --- |
| Nucleotide sequence | gaagttaagctgcaggagtcaggggcagagcttgtgaagccaggggcctcagt caagttgtcctgcacagtttctggcttcaacattaaagacacctatatacact gggtgatacagaggcctgaacagggcctggagtggcttggaaggattgatcct gcgaatggtaatactaaatatgacccgaagttccagggcaaggccactataac agcagacacatcctccaacacagcctacctgcagctcagcagcctgacctctg aggacactgccgtctattactgtgctagatgggcggttgtaggtgactactgg ggccaaggcaccactctcacagtctcctcag (SEQ ID No. 1) |
| Peptide sequence | EVKLQESGAELVKPGASVKLSCTVSGFNIKDTYIHWVIQRPEQGLEWLGRIDP ANGNTKYDPKFQGKATITADTSSNTAYLQLSSLTSEDTAVYYCARWAVVGDYW GQGTTLTVSS (SEQ ID No. 2) |

| Light chain (V-J region) |
| --- |

| | |
| --- | --- |
| Nucleotide sequence | gatattgtgatcacccactctacaaattcctgcatgtatcagcaggagacagg gttaccataacctgcaaggccagtcagagtgtgagtgatgatgtggcttggta ccaacagaagccagggcagtctcctaaactgctgatatactctgcatccaatc gctacactggagtccctgatcgcttcactggcagtggatatgggacggatttc actttcaccatcagcactgtgcagcctgaagacctggcagtttatttctgtca gcaggattatagctctcccacgttcggttctgggaccaagctggagctgaaac (SEQ ID No. 3) |
| Peptide sequence | YCDHPLYKFLHVSAGDRVTITCKASQSVSDDVAWYQQKPGQSPKLLIYSASNR YTGVPDRFTGSGYGTDFTFTISTVQPEDLAVYFCQQDYSSPTFGSGTKLELK (SEQ ID No. 4) |

TABLE 2

| ITAC-B2 |
| --- |
| Heavy chain (V-D-J region) |

| | |
| --- | --- |
| Nucleotide Sequence | gaggtgcagctggaggagtcaggggggaggcttagtgaagcctggagggtccct gaaactctcctgtgcagcctctggattcactttcagtgactattacatgtatt gggttcgccagactccggaaaagaggctggagtgggtcgcaaccattagtgat ggtggtagttacacctactatccagacagtattaagggccgattcaccatctc cagggacaatgccaggaacaacctgtacctttcaaatgagcagtctgaagtctg aggacacagccatgtattactgtgcaagaggtgggccctataggtcctggtttt gctttctggggccaagggactctggtcactgtctctgcag (SEQ ID No. 5) |
| Peptide sequence | EVQLEESGGGLVKPGGSLKLSCAASGFTFSDYYMYWVRQTPEKRLEWVATISD GGSYTYYPDSIKGRFTISRDNARNNLYLQMSSLKSEDTAMYYCARGGPYRSWF AFWGQGTLVTVSA (SEQ ID No. 6) |

| Light chain (V-J region) |
| --- |

| | |
| --- | --- |
| Nucleotide sequence | gatattgtgatcacccagactccactctccctgcctgtcagtcttggagatca agcctccatctcttgcagatctagtcagagcattgtgtatagtaatggaaaca cctatttagaatggtacctgcagaaaccaggccagtctccaaagctcctgatc tacaaagtttccaaccgattttctggggtcccagacaggttcagtggcagtgg atcagggacagatttcacactcaagatcagcagagtggaggctgaggatctgg gagtttattactgctttcaaggttcacatgttcctccgacgttcggtggaggc accaagctggaaatcaaac (SEQ ID No. 7) |
| Peptide sequence | DIVITQTPLSLPVSLGDQASISCRSSQSIVYSNGNTYLEWYLQKPGQSPKLLI YKVSNRFSGVPDRFSGSGSGTDFTLKISRVEAEDLGVYYCFQGSHVPPTFGGG TKLEIK (SEQ ID No. 8) |

The sequences encoding the CDRs of ITAC-B1 and ITAC-B2 have also been determined, from the sequences of the heavy chains and of the light chains above, using the IMGT/V-QUEST software (Giudicelli et al., Nucleic Acids Research 32, W435-W440, 2004). The deduced polypeptide sequences are represented below in Table 3 for the ITAC-B1 antibody, and Table 4 for the ITAC-B2 antibody. They are also represented in the sequence listing in annex under the numbers SEQ ID No. 9 to 20.

TABLE 3

| ITAC-B1 | Sequence |
|---|---|
| Heavy chain | |
| VH-CDR1 | GFNIKDTY (SEQ ID No. 9) |
| VH-CDR2 | IDPANGNT (SEQ ID No. 10) |
| VH-CDR3 | ARWAVVGDY (SEQ ID No. 11) |
| Light chain | |
| VL-CDR1 | QSVSDD (SEQ ID No. 12) |
| VL-CDR2 | SAS (SEQ ID No. 13) |
| VL-CDR3 | QQDYSSPT (SEQ ID No. 14) |

TABLE 4

| ITAC-B2 | Sequence |
|---|---|
| Heavy chain | |
| VH-CDR1 | GFTFSDYY (SEQ ID No. 15) |
| VH-CDR2 | ISDGGSYT (SEQ ID No. 16) |
| VH-CDR3 | ARGGPYRSWFAF (SEQ ID No. 17) |
| Light chain | |
| VL-CDR1 | QSIVYSNGNTY (SEQ ID No. 18) |
| VL-CDR2 | KVS (SEQ ID No. 19) |
| VL-CDR3 | FQGSHVPPT (SEQ ID No. 20) |

The antibodies comprising the variable domains of ITAC-B1 (i.e. comprising a heavy chain of which the variable domain is defined by the sequence SEQ ID No. 2 and a light chain of which the variable domain is defined by the sequence SEQ ID No. 4) or the variable domains of ITAC-B2 (i.e. comprising a heavy chain of which the variable domain is defined by the sequence SEQ ID No. 6 and a light chain of which the variable domain is defined by the sequence SEQ ID No. 8), and also the antibodies or antibody-derived ligands, as defined above, comprising at least the CDR3s of ITAC-B1 or of ITAC-B2, constitute preferred embodiments of the subject of the present invention.

A subject of the present invention is also any polynucleotide encoding an antibody in accordance with the invention or encoding a ligand of human neuropilin-2 derived from said antibody, and also a recombinant vector, in particular an expression vector, containing said nucleotide. A subject of the present invention is also cells which produce antibodies or antibody derivatives in accordance with the invention. They may in particular be hybridomas, for example the CNCM I-4054 hybridoma, and host cells transformed with an expression vector in accordance with the invention. Said host cell may be a prokaryotic or eukaryotic cell. Among the eukaryotic cells that can be used, mention may in particular be made of plant cells, yeast cells, such as *Saccharomyces*, insect cells, such as the cells of *Drosophila* or of *Spodoptera*, and mammalian cells such as HeLa, CHO, 3T3, C127, BHK, COS, etc, cells.

The construction of the expression vectors in accordance with the invention, and the transformation of the host cells, can be carried out by means of conventional molecular biology techniques.

A subject of the present invention is also an anti-human neuropilin-2 antibody in accordance with the invention, or a ligand of human neuropilin-2 derived from said antibody, for use as a medicament, in particular as an antitumour medicament.

According to one preferred embodiment of the present invention, said medicament is intended to induce apoptosis of tumour cells expressing neuropilin-2, in particular by increasing p53 expression in said tumour cells.

The invention is applicable to all types of tumours expressing neuropilin-2, and in particular to colorectal cancers, to breast cancers, to kidney cancer and to melanomas. The expression of neuropilin-2 in a tumour can readily be detected, for example using anti-human neuropilin-2 antibodies.

For the implementation of the present invention, the anti-human neuropilin-2 antibody or the ligand of human neuropilin-2 in accordance with the invention may be administered intravenously, intraarterially or intraperitoneally.

Advantageously, it may be administered in combination with another antitumour agent.

Antitumour agents that can be used in combination with an anti-human neuropilin-2 antibody or a ligand of human neuropilin-2 in accordance with the invention are in particular chemotherapy agents (such as alkylating agents, nucleotide analogues or topoisomerase inhibitors), ionizing radiation or biotherapies (in particular targeted therapeutic molecules neutralizing, for example, VEGF, or the EGF receptor, tyrosine kinase inhibitors or inhibitors of the mTor pathway).

The present invention will be understood more clearly from the further description which follows, which refers to nonlimiting examples illustrating the effect of the inhibition of NRP-2 with siRNA on p53 expression, and tumour cell apoptosis, and the preparation of anti-NRP-2 antibodies reproducing these effects.

EXAMPLE 1

Generation of Cell Lines Exhibiting Human Neuropilin-2 at their Membrane Surface Two cell lines were transfected in order to express NRP-2 at their surface. A murine line, the P815 mastocytoma (Diaclone), which is an experimental tumour widely used as a model in tumour immunology, and which does not naturally express human NRP-2, and also a human tumour line, developed from HT29 colorectal cancer cells, not naturally expressing NRP-2 at its membrane surface, were transfected with a human-NRP-2 expression vector. The expression vector used, based on a plasmid pcDNA3.1 (Invitrogen) has been described by Rossignol M et al, (Genomics. 2000 Dec. 1; 70(2):211-22).

The transfect p815 murine line was used to produce murine monoclonal antibodies directed against the human NRP-2 glycoprotein, and the transfected human line was then used in functional experiments for evaluating the advantage of the anti-NRP-2 antibodies.

The transfection of the lines was carried out using an Effecten® kit (Qiagen). The P815 mastocytes and the HT29 tumour cells were cultured in 20 ml of DMEM medium until a concentration of 200 000 cells/ml was reached. The cells were then washed once with 20 ml of PBS and brought to a concentration of $2 \times 10^5$ cells/ml in 4 ml of DMEM medium in a flask. The cells were then transfected with 1 µg of vector (plasmid vector at 1 µg/µl in TBE buffer).

The transfected P815 and HT29 cells were left in small flasks and incubated at 37° C. under 5% $CO_2$ in a humidified atmosphere, for 48 h. At D3, the culture media were replaced with a new medium containing 0.8 mg/ml of geneticin (G418, Invitrogen, France), for selection of the transfected cells.

The efficiently transfected cells expressing NRP-2 at their surface are called P815-NRP-2 and HT29-NRP-2. The efficiency of transfection is evaluated at D7 by membrane labelling with a murine anti-human NRP-2 IgG antibody (Clone C9, Santa Cruz Biotechnology) and then reading by flow cytometry. The result of the flow cytometry study is represented in FIG. 1.

Panels A and C (P815 and HT29ctrl) of FIG. 1 represent the results obtained by flow cytometry with the control cells, while panels B and D (P815-NRP-2 and HT29-NRP-2) represent the results obtained with cells expressing NRP-2 at their membrane surface. The distribution curves in black lines represent the results of the labelling with a control antibody, the distribution curves in grey lines represent the results of the labelling with the murine anti-human NRP-2 IgG antibody.

For each of the panels of FIG. 1, the number of events (number of cells) is indicated on the y-axis, the fluorescence intensity (corresponding to the labelling of the cells with the murine anti-human NRP-2 IgG antibody) is represented on the x-axis. Panels A and C (P815 and HT29ctrl) of FIG. 1 show that the distribution peaks representing the P815 and HT29ctrl cell population (noninfected controls) in contact with the anti-human NRP-2 antibody (grey line) or with a control IgG antibody (black line) superimposed: this signifies that the P815 and HT29ctrl cells (noninfected controls) are no more heavily labelled with the anti-human NRP-2 antibody than with a control IgG antibody and that they do not therefore express NRP-2. On the other hand, when the P815 and HT29 cells transfected with a human-NRP-2 expression vector (panels B and D, P815-NRP-2 and HT29-NRP-2, respectively) are brought into contact with the anti-human NRP-2 antibody, there is a clear shift in the cell-population distribution peak towards the right (grey-line peak) relative to the labelling with the control IgG antibody (black-line peak). These results attest to the fact that the transfected cells clearly express NRP-2 at their membrane surface.

EXAMPLE 2

Production and Characterization of Anti-Human NRP-2 Monoclonal Antibodies

An immunization protocol derived from that described by Matthew and Sandrock (J. Immunol. Methods, 100: 73-82, 1987) was used. In each experiment, five female Balb/C mice (Charles River Laboratories) were immunized with P815-NRP-2 transfected cells once a week for 5 weeks.

Each immunization consists of the administration, in the "foot-pad", of $1 \times 10^6$ P815-NRP-2 cells in each back foot of the mouse (i.e. $2 \times 10^6$ P815-NRP-2 per mouse). The cells used for the immunization of a mouse were diluted in 25 µl of 1×PBS and in 25 µl of Ribi adjuvant (Immunochem Research, USA). 50 µl of cell mixture were then injected into each mouse (25 µl per back foot) several times during the immunization protocol. Five days after the final injection, the lymph nodes of the mice were removed and the lymphocytes were fused with a myeloma line. The fusion was carried out in the following way: the lymphocytes removed were fused with X63/AG 8653 murine myeloma cells (the lymphocyte/myeloma cell ratio is 5:1), in the presence of polyethylene glycol (Kearney et al, J. of Immunol, 123: 1548, 1978). The P3×63/AG8.653 murine myeloma originates from the ATCC (ref CRL-1580).

The suspension of fused cells was washed once, and cultured on a selective medium composed of 500 ml of RPMI 1640 (Sigma, France), supplemented with 10% of heat-inactivated FCS (Abcys, France), 4 mM of L-glutamine (Sigma, France), 100 mg/ml of streptomycin, 100 IU/ml of penicillin (Sigma, France), 13.6 µg/ml of hypoxanthine, 0.19 mg/ml of aminopterin and 3.88 IU/ml of thymidine (50× solution, Sigma, France). This medium allows neither the survival of the myeloma cells that have not fused, since the latter are incapable of synthesizing inositol monophosphate, nor the survival of the lymphocytes, which do not have the ability to multiply indefinitely in vitro. On the other hand, the hybridomas survive because they have, on the one hand, the ability to metabolize the exogenous hypoxanthine (property of lymphocytes) and, on the other hand, the ability to multiply indefinitely ("immortality") of the X63/AG 8653 cells.

Ten days after the fusion, the supernatants from the cultures in which hybridoma growth was observed were tested in order to detect the production of anti-NRP-2 monoclonal antibodies. For this purpose, the supernatants of each hybridoma culture well were tested by flow cytometry on the cell lines expressing or not expressing neuropilin-2.

The hybridomas producing antibodies recognizing the P815-NRP-2 line were cloned using the limiting dilution method (seeding density of 1 cell per culture well).

Several candidates specifically recognizing NRP-2 were generated and selected for their ability to induce apoptosis of tumour cells expressing neuropilin-2, including the clones ITAC-B1 and ITAC-B2. The ITAC-B1 clone was deposited, according to the Treaty of Budapest, with the CNCM (Collection Nationale des Microorganismes [French National Microorganism Collection], Institut Pasteur, 25 rue du Docteur Roux, 75724 Paris Cedex 15, France) on 30 Jul. 2008 under the deposit number CNCM I-4054. In order to characterize the ITAC-B1 and ITAC-B2 monoclonal antibodies, membrane labelling was carried out by flow cytometry by bringing 200 000 HT29, HT29-NRP-2, P815 or P815-NRP-2 cells into contact with 5 µg/ml of ITAC-B1 or of ITAC-B2, for 15 minutes at 4° C. A goat anti-mouse secondary antibody coupled to FITC was then incubated for 15 minutes in the dark, at 4° C., before reading by flow cytometry. The results of the flow cytometry analysis obtained for ITAC-B1 are represented in FIG. 2.

Figure 2:
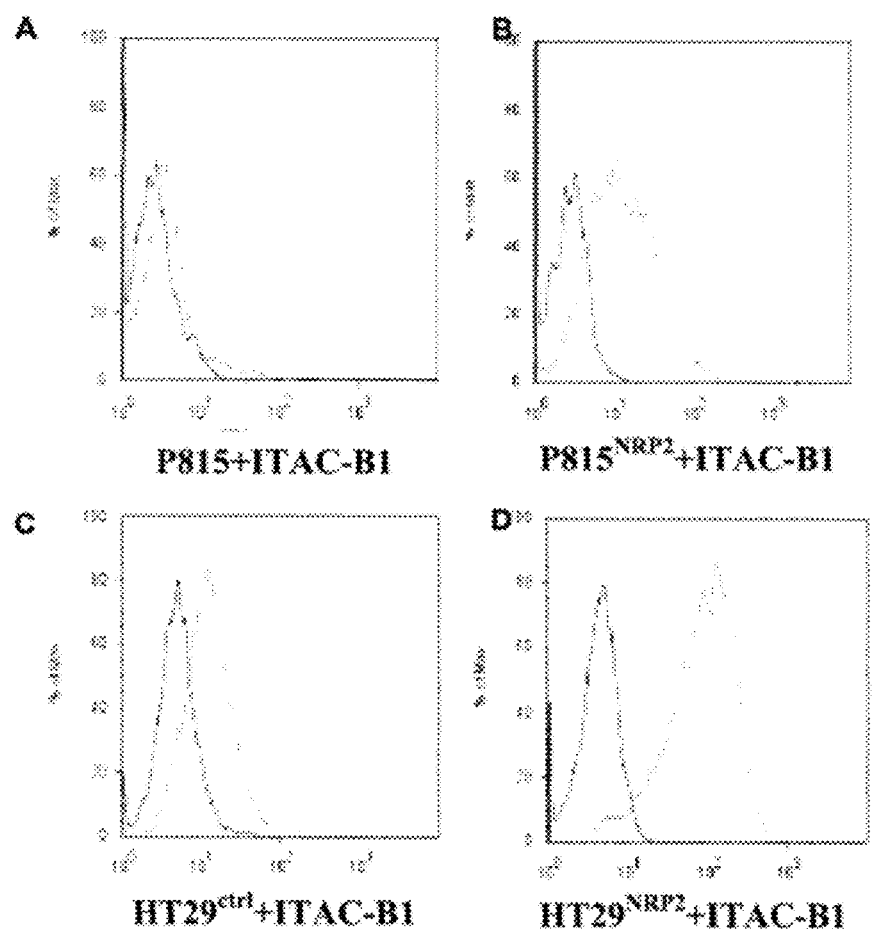
FIG. 2 illustrates the results of a flow cytometry analysis obtained for ITAC-B1 where panels A and C represent the results obtained by flow cytometry with control cells, while panels B and D represent the results obtained with cells expressing NRP-2 at their membrane surface.

For each of the panels of FIG. 2, the number of events (number of cells) is indicated on a y-axis, the fluorescence intensity (corresponding to the labelling of the cells with the ITAC-B1 antibody) is represented on the x-axis. Panels A and C (P815+ITAC-B1 and HT29ctrl+ITAC-B1) of FIG. 2 represent the results obtained by flow cytometry with the control cells, while panels B and D (P815-NRP-2+ITAC-B1 and HT29-NRP-2+ITAC-B1) represent the results obtained with cells expressing NRP-2 at their membrane surface. The distribution curves in black lines represent the results of the labelling with a control antibody, the distribution curves in grey lines represent the results of the labelling with the ITAC-B1 antibody. For cell lines expressing NRP-2, a clear shift in the cell-population distribution peak towards the right is noted when there is labelling with ITAC-B1 (grey line), in comparison with the labelling with the control IgG antibody (black line). For the cell lines not expressing NRP-2, this shift in the distribution peak is very slight. These results show that the ITAC-B1 antibodies specifically recognize the neuropilin-2 present at the membrane surface.

Similar results were obtained for the ITAC-B2 antibody.

The genomic sequences of the variable region of the heavy chains of the hybridomas producing the ITAC-B1 and ITAC-B2 antibodies were analysed by sequencing, respectively, with the primers:

```
(degenerate sense primer)
                                        (SEQ ID No. 21)
5'-GARGTTAAGCTGSAGGAGTCAGG-3'

(antisense primer)
                                        (SEQ ID No. 22)
5'-ATAGACAGATGGGGGTGTCGTTTTGGC-3';
and (sense primer)
                                        (SEQ ID No. 23)
5'-GAGGTGCAGCTGGAGGAGTCAGG-3'

(antisense primer)
                                        (SEQ ID No. 24)
5'-ATAGACAGATGGGGGTGTCGTTTTGGC-3'.
```

The genomic sequences of the variable region of the heavy chains of the hybridomas producing the ITAC-B1 and ITAC-B2 antibodies were analysed by sequencing, respectively, with the primers:

```
(degenerate sense primer)
                                        (SEQ ID No. 25)
5'-GATATTGTGATSACMCARDCTACA-3'

(antisense primer)
                                        (SEQ ID No. 26)
5'-GGATACAGTTGGTGCAGCATTA-3';
and (degenerate sense primer)
                                        (SEQ ID No. 27)
5'-GATATTGTGMTSACCCAGACTCCA-3'

(antisense primer)
                                        (SEQ ID No. 28)
5'-GGATACAGTTGGTGCAGCATTA-3'.
```

The amino acid sequences of the CDR1, CDR2 and CDR3 hypervariable loops of the variable regions of the ITAC-B1 and ITAC-B2 antibodies were determined using the IMGT/V-QUEST software, version 3.0.0, on the immunoglobulin database of "the international ImMunoGeneTics Information System®" (IMGT/GENE-DB).

EXAMPLE 3

Role of Neuropilin-2 in Cell Proliferation

Production of a Vector Expressing Double-Stranded siRNAs Targeting the Human NRP-2 Gene A sense oligonucleotide: 5'-AAA GGC TGG AAG TCA GCA CTA AT-3' (SEQ ID No. 29), and an antisense oligonucleotide: 5'-AAA AAT TAG TGC TGA CTT CCA GC-3' (SEQ ID No. 30) corresponding to a part of the gene sequence of human NRP-2, were hybridized, and the resulting duplex was inserted into a dual-promoter expression vector (pFiv H1/U6puro SiRNA Expression vector, System Biosciences) digested beforehand with the BbsI enzyme.

After having verified that the insert indeed had the expected size (21 base pairs), 100 µl of competent E. coli HB101 bacteria (Gibco) were transformed with 1 µg of the vector containing this insert. A colony was amplified in 200 ml of LB medium with ampicillin using a high-speed midi prep kit (Qiagen), and then a maxiprep (Qiagen) was carried out and resulted in the purification of the plasmid pFiv H1/U6puro SiRNA-NRP-2.

Since the plasmid pFiv H1/U6puro SiRNA-NRP-2 contains the H1 and U6 promoters of RNA polymerase III boarding the insert, each of the strands of the insert is transcribed in the cells transfected with this plasmid, resulting in the generation of double-stranded siRNA directed against the NRP-2 transcripts, constituted of:

```
sense strand:
                                        (SEQ ID No. 31)
5'-GGC UGG AAG UCA GCA CUA AUU U-3';

antisense strand:
                                        (SEQ ID No. 32)
5'-AUU AGU GCU GAC UUC CAG CCU U-3'.
```

Production of a Cell Line Expressing an siRNA Targeting the Human NRP-2 Gene

The Colo320 line naturally expressing neuropilin-2 at its membrane surface was transfected with the plasmid pFiv H1/U6puro siRNA-NRP-2 using the Effectene® kit, Qiagen). In parallel, Colo320 cells were transfected with a control siRNA (siRNA-ctrl) provided with the pFiv H1/U6puro SiRNA expression vector kit (System Biosciences). The Colo320$^{siRNA-NRP-2}$ and Colo320$^{siRNA-ctrl}$ transfected cells were then selected at D2 with 2 µg/ml of puromycin. The efficiency of the transfection was evaluated from D7 onwards by labelling with a murine anti-human NRP-2 IgG antibody (Clone C9, Santa Cruz Biotechnology) by flow cytometry: the results obtained are represented in FIG. 3.

Figure 3:
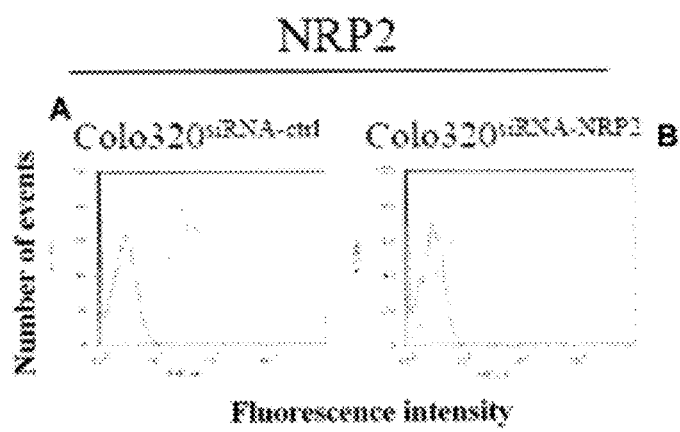
FIG. 3 illustrates the results of labelling with a murine anti-human NRP-2 IgG antibody by flow cytometry where panel B, which represents the analysis carried out with Colo320$^{siRNA-NRP-2}$ cells naturally expressing NRP-2, shows a shift towards the left of the distribution peak for the cells labelled with the C9 antibody, compared with the analysis carried out with Colo320 $^{siRNA-ctrl}$ cells, which is represented on panel A.

For each of the panels of FIG. 3, the number of events (the number of cells) is indicated on the y-axis, the fluorescence intensity (corresponding to the label of the cells with the anti-NRP-2 antibody C9) is represented on the x-axis. The distribution curves in black lines represent the results obtained after labelling with a control antibody, the distribution curves in grey lines represent the results obtained after labelling with the C9 antibody. Panel B of FIG. 3, which represents the analysis carried out with the Colo320$^{siRNA-NRP-2}$ cells naturally expressing NRP-2, shows a shift towards the left of the distribution peak for the cells labelled with the C9 antibody, compared with the analysis carried out with the Colo320$^{siRNA-ctrl}$ cells, which is represented on panel A.

These results show that the expression of the NRP-2 protein is efficiently inhibited in the cells expressing the siRNA-NRP-2.

Assay for Proliferation in the Presence of siRNA-NRP-2: MTT Test

The MTT proliferation assay is based on the reduction of 3-(4,5-dimethylthiazol-2-yl)-2,5-diphenyltetrazolium bromide), by the mitochondrial succinate dehydrogenase of active live cells, to give formazan. The coloration intensity (OD) induced by this reaction is proportional to the number of live cells present during the assay, and to the metabolic activity thereof.

4000 HT29ctrl, HT29-NRP-2, Colo320$^{siRNA-ctrl}$ or Colo320$^{siRNA-NRP-2}$ cells were seeded into a 96-well Maxisorp plate, in 100 µl of DMEM medium containing 10% of inactivated FCS. The assay was carried out in triplicate. At 24, 48 and 72 hours, respectively, 10 µl of MTT at 5 mg/ml were added to each well. After 2 hours of incubation at 37° C., 5%

$CO_2$, 200 µl of DMSO were added to each well after shaking, and the OD was read at 570 nm using a spectrophotometer. The results of these experiments are represented in FIG. 4.

Figure 4:
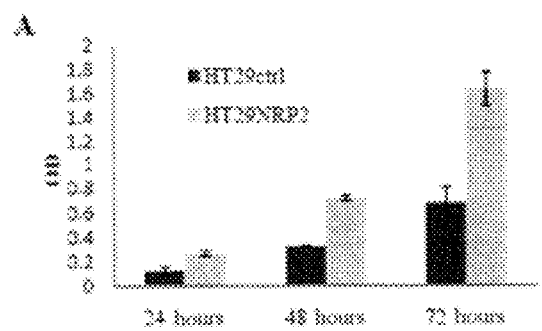
FIG. 4 illustrates histograms representing the results obtained in a proliferation assay carried out respectively with panel A showing HT29ctrl and HT29-NRP-2 cells and with panel B showing Colo320$^{siRNA-ctrl}$ and Colo320$^{siRNA-NRP-2}$ cells.
Figure 4:
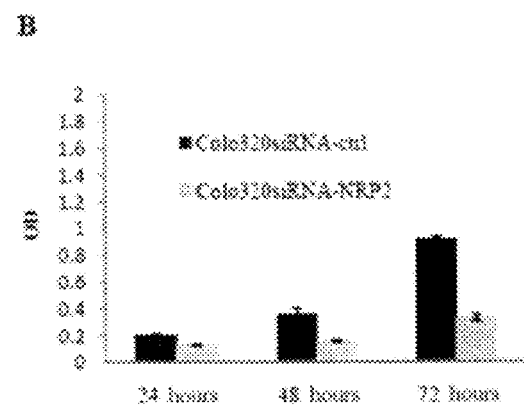

FIGS. 4.A and 4.B are histograms representing the results obtained in the proliferation assay carried out respectively with the HT29ctrl and HT29-NRP-2 cells and with the Colo320$^{siRNA-ctrl}$ and Colo320$^{siRNA-NRP-2}$ cells. The coloration intensity (the optical density "OD") corresponding to the production of formazan by the cells is indicated on the y-axis, and the times at which the viability tests were carried out are indicated on the x-axis. For panel A, the light grey bars represent the measurements carried out on the HT29-NRP-2 cells, and the dark grey bars represent the measurements carried out on the HT29ctrl control cells. For panel B, the light grey bars represent the measurements carried out on the Colo320$^{siRNA-NRP-2}$ cells, the NRP-2 expression of which is suppressed, and the dark grey bars represent the measurements carried out on the Colo320$^{siRNA-ctrl}$ control cells expressing NRP-2.

FIG. 4.A shows that the OD increases when the cells express NRP-2, which signifies that the expression of NRP-2 by the HT29-NRP-2 cells induces cell proliferation and survival greater than that of the cells not expressing NRP-2.

FIG. 4.B shows that the OD decreases when the NRP-2 expression in the Colo320 cells is suppressed (cf. bars representing Colo320$^{siRNA-NRP-2}$ in comparison with Colo320$^{siRNA-ctrl}$). This result confirms the result obtained with the HT29 cells: NRP-2 induces a greater cell proliferation and survival in the cells.

The influence of neuropilin-2 on the cell cycle was studied. 50 000 HT29 or HT29-NRP-2 cells were seeded, in 1 ml of DMEM-10% FCS, in a 2-well plate. 24 hours after seeding, the cells were trypsinized, washed twice with 3 ml of PBS and taken up in 1 ml of 70% ethanol. They were left at 4° C., in 70% ethanol, overnight. The following day, the cells were washed twice with 3 ml of PBS, digested with Dnase and labelled with PI. 30 min later, the cells were analysed using an EPIC'C Altra cytometer (Beckman Coulter) and the Wincycles cycle analysis software. The results of this analysis are given in FIG. 4bis.

FIG. 4bis shows that, when the cells express NRP-2, the number of cells in G2M and S phase increases, whereas the number of cells in G1 decreases. Thus, neuropilin-2 expression is associated with an increase in the fraction of cells in S and G2M phase.

The oncogenic influence of neuropilin-2 was also evaluated by comparing, in mice, the development of xenografts of various tumour lines as a function of the expression of neuropilin-2 in these lines.

Figure 5:
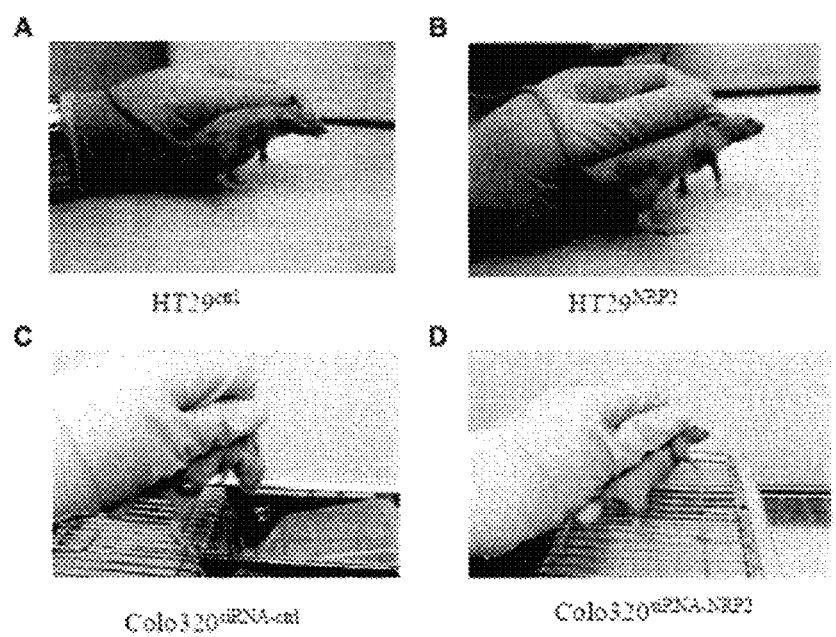
FIG. 5 illustrates photographs of mice inoculated subcutaneously with panel A showing HT29ctrl, panel B showing HT29-NRP-2, panel C showing Colo320$^{siRNA-ctrl}$ and panel D showing Colo320$^{siRNA-NRP-2}$ cells.

FIGS. 5.A, 5.B, 5.C and 5.D are photographs of mice having been inoculated subcutaneously with the HT29ctrl, HT29-NRP-2, Colo320$^{siRNA-ctrl}$ and Colo320$^{siRNA-NRP-2}$ cells, respectively.

While in mice inoculated with cells not expressing NRP-2 (FIG. 5.A and FIG. 5.D), there is no abnormal progression of the xenograft, an abnormal increase in proliferation of the xenograft is observed in the mice inoculated with cells expressing NRP-2 (FIG. 5.B and FIG. 5.C). These experiments show that the expression of neuropilin-2 after transfection, or the repression of this protein by interfering RNA, influences the oncogenesis of the lines.

Modulation of p53 Expression with an siRNA Targeting the Human NRP-2 Gene

The expression of p53, of E-cadherins and of cytokeratin 20 in xenografts of tumour cells expressing or not expressing neuropilin-2 (HT29ctrl or HT29-NRP-2 line) was studied by immunohistochemistry using antibodies specific for each of these three proteins.

Figure 6:
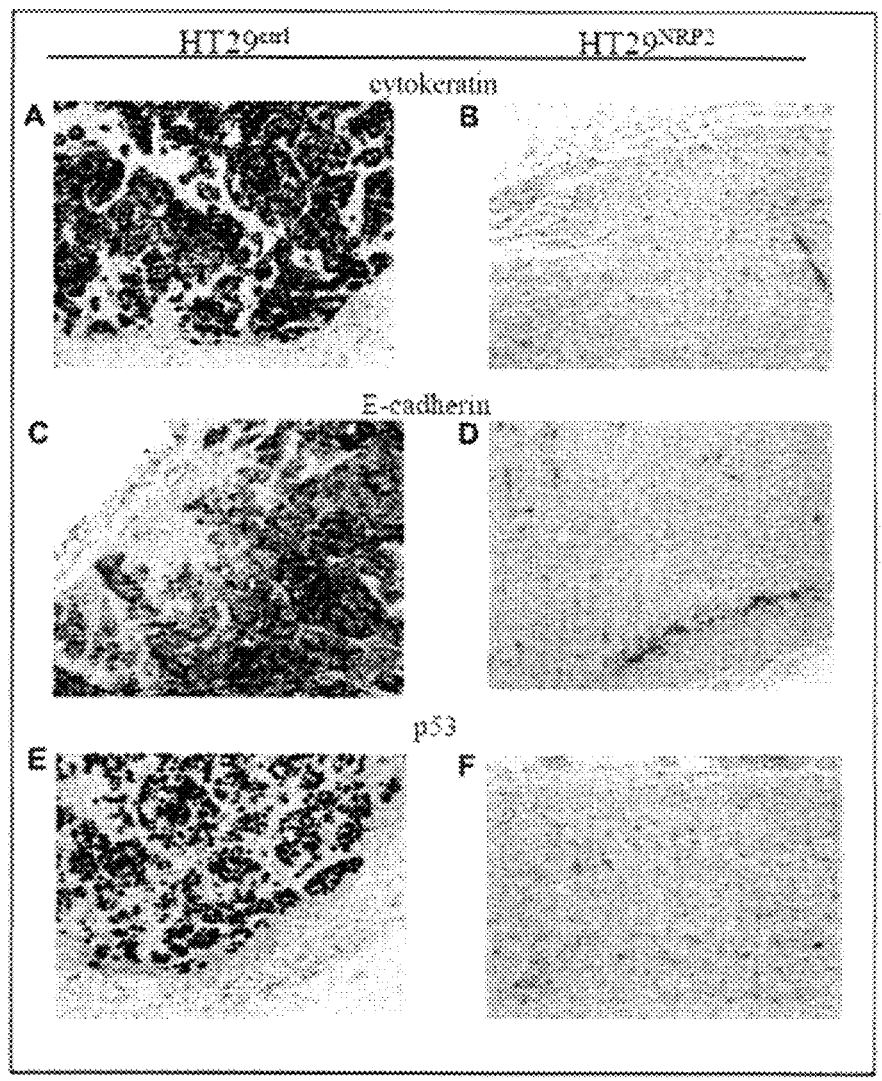
FIG. 6 illustrates photographs of sections of xenografts taken in mice, where panels A, C and E show mice inoculated with a HT29ctrl control line, and panels B, D and F show mice inoculated with a line expressing NRP-2 (HT29-NRP-2).

FIGS. 6.A, 6.C and 6.E are photographs of sections of xenografts taken in mice inoculated with the HT29ctrl control line, and FIGS. 6.B, 6.D and 6.F are photographs of sections of xenografts taken in mice inoculated with the line expressing NRP-2 (HT29-NRP-2).

The sections of xenografts of FIGS. 6.A and 6.B were labelled with an anti-cytokeratin antibody, the sections of xenografts of FIGS. 6.C and 6.D were labelled with an anti-E-cadherin antibody, and the sections of xenografts of FIGS. 6.E and 6.F were labelled with an anti-p53 antibody.

FIGS. 6.A, 6.C and 6.E show that the xenografts derived from the HT29ctrl control line are strongly labelled with the anti-cytokeratin, anti-E-cadherin and anti-p53 antibodies, whereas the xenografts derived from the HT29-NRP-2 control line are not labelled with any of these antibodies.

This study showed that the transfection of neuropilin-2, which promotes xenograft progression (FIGS. 5.A to 5.D), is associated with a loss of expression of the p53 anti-oncogene in the nuclei of the tumour cells (FIG. 6). In addition, the immunohistochemical study shows a loss of E-cadherin and cytokeratin 20 expression in the xenografts expressing neuropilin-2 (FIG. 6), suggesting that the acquisition of neuropilin-2 would promote epithelio-mesenchymal transition.

The influence of neuropilin-2 on p53 expression was also studied. For this, the HT29-NP-2 or Colo320 lines were treated either with siRNAs that inhibit the translation of neuropilin-2, or with monoclonal antibodies originating from the ITAC-B1 hybridoma.

Figure 7:
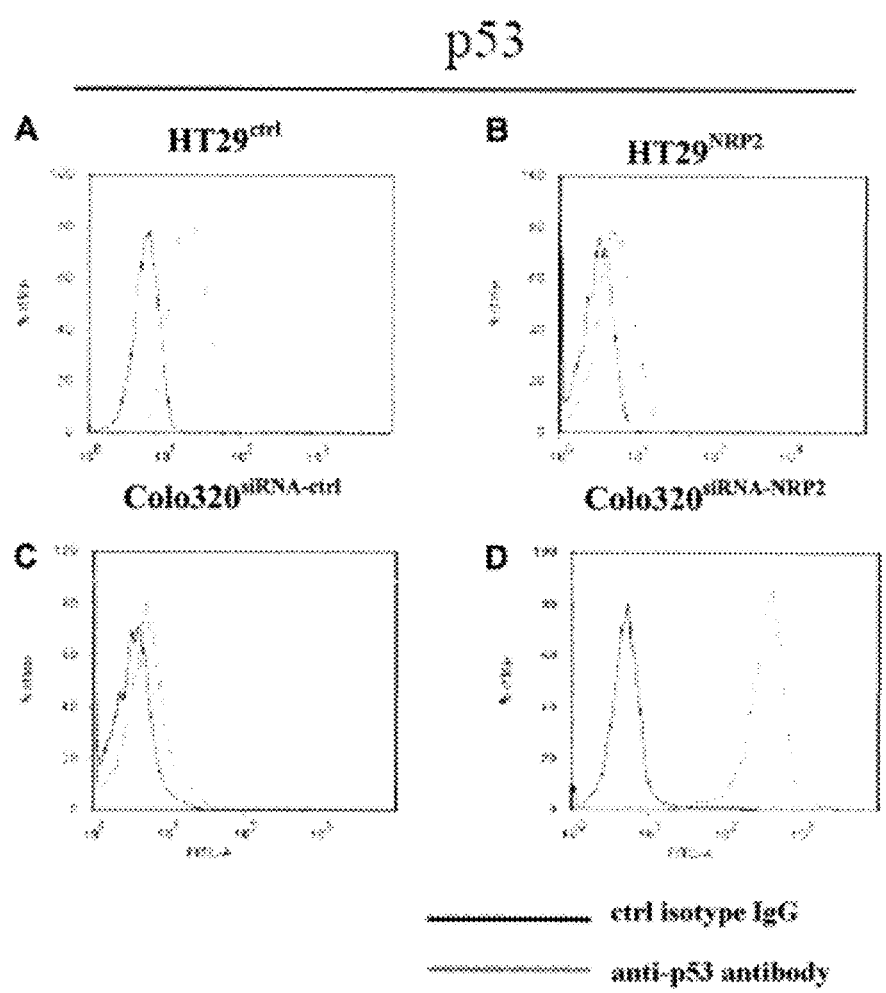
FIG. 7 represents the results obtained by flow cytometry for HT29-ctrl (panel A), HT29-NRP-2 (panel B), Colo320$^{siRNA-ctrl}$ (panel C) and Colo320$^{siRNA-NRP-2}$ (panel D) cells labelled with an anti-p53 antibody.

FIG. 7 represents the results obtained by flow cytometry for the HT29-ctrl (panel A), HT29-NRP-2 (panel B), Colo320$^{siRNA-ctrl}$ (panel C) and Colo320$^{siRNA-NRP-2}$ (panel D) cells labelled with an anti-p53 antibody. The curves in black lines represent the results of the labelling with a control antibody, and the curves in grey lines represent the results of the labelling with the anti-p53 antibody. The number of events (the number of cells) is indicated on the y-axis, the fluorescence intensity (corresponding to the labelling of the cells with the anti-p53 antibody) is represented on the x-axis.

Panels B and C showing the results obtained for the lines expressing NRP-2, i.e. the panels HT29-NRP-2 and Colo320$^{siRNActrl}$, show that the p53 protein is not expressed or is expressed very little (the curves of the populations labelled with the control antibody or the anti-p53 antibody superimposed). On the other hand, as regards panels A and D which show the results obtained for the lines not expressing the NRP-2 protein, i.e. the panels HT29ctrl and Colo320$^{siRNA-NRP-2}$, when labelling is carried out with the anti-p53 antibody (grey line), there is a shift in the cell-population distribution peak towards the right, in comparison with the labelling with control IgG antibody (black line).

These experiments show that a negative correlation exists between the presence of neuropilin-2 and that of p53. In particular, when colo320, which is a tumour line constitutively expressing neuropilin-2, is treated with interfering RNA so as to inhibit the translation of this protein (Colo320$^{siRNA-NRP-2}$ lines), restoration of p53 expression in the tumour lines is clearly observed.

The protein extracts of the HT29-ctrl, HT29-NRP-2, Colo320$^{siRNA-ctrl}$ and Colo320$^{siRNA-NRP-2}$ lines were also analysed by Western blotting using an anti-p53 antibody. After lysis of the cell lines, migration of the protein pellets obtained on a 10% polyacrylamide gel (10 µg of protein per well, standardized relative to the immunoblotting of actin), and then transfer onto a PVDF membrane, the PVDF membrane was incubated overnight with the p53 primary antibody (BD Biosciences, mouse anti-human p53) diluted to 1/500. The membranes, after washing in TBS/0.1% Tween20, were incubated for 1 hour with an anti-mouse HRP secondary antibody diluted to 1/12 500. The results are represented in FIG. 8.

Figure 8:
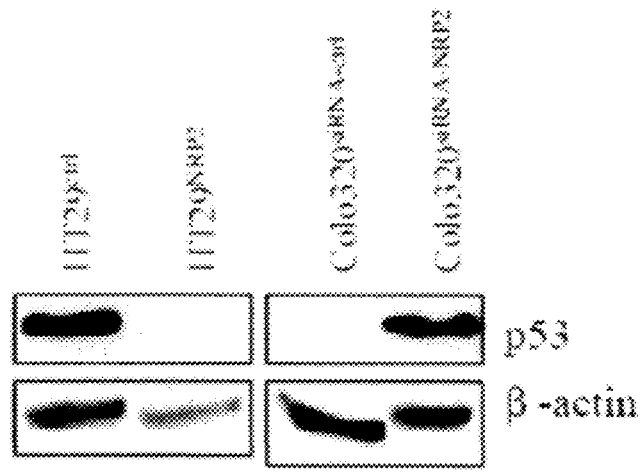
FIG. 8 represents the results obtained with PVDF membranes incubated with an anti-mouse HRP secondary antibody, and shows that the p53 protein is strongly expressed in a HT29-ctrl line not expressing NRP-2 and in the Colo320$^{siRNA-NRP-2}$ line in which the expression of NRP-2 is repressed.

FIG. 8 shows that the p53 protein is strongly expressed in the HT29-ctrl line not expressing NRP-2, whereas it is undetectable in the HT29-NP-2 line. Similarly, p53 cannot be demonstrated in the Colo320$^{siRNA-ctrl}$ line which expresses NRP-2, whereas it is strongly expressed in the Colo320$^{siRNA-NRP-2}$ line in which the expression of NRP-2 is repressed.

This experiment confirms that a negative correlation exists between the presence of neuropilin-2 and the expression of p53.

These data indicate that the inhibition of neuropilin-2 expression makes it possible to increase p53 expression.

EXAMPLE 4

Effect of the ITAC-B1 Antibody on Tumour Cell Growth

Test for Formation of Tumour Colonies in a Semi-Solid Agar Medium

In order to determine whether the ITAC-B1 antibody has a neutralizing activity on the formation of tumour colonies in vitro, tests for tumour colony formation in vitro in a semi-solid agar medium containing agar were carried out. The principle of this test is based on bringing Colo320 human tumour cells (which express NRP-2 at their membrane surface and, furthermore, naturally secrete VEGF into the culture medium) into contact with the ITAC-B1 antibody. 4000 Colo320 cells are seeded into each well of a 24-well plate, in a semi-solid medium containing agar, and in the presence of 10 µg/ml of anti-NRP-2 antibody ITAC-B1. By way of comparison, the same test is carried out in the presence of cytotoxic agents with a proven action, i.e. 5-fluorouracil (5-FU), used at a rate of 50 µg/ml, or of Avastin® (bevacizumab: humanized monoclonal antibodies directed against VEGF), used at a rate of 50 µg/ml, or in the presence of a control isotype antibody (mouse IgG1 monoclonal antibody (BZ1)), used at a rate of 10 µg/ml.

At 10 days post-seeding, the colonies were counted under an optical microscope.

Figure 9:
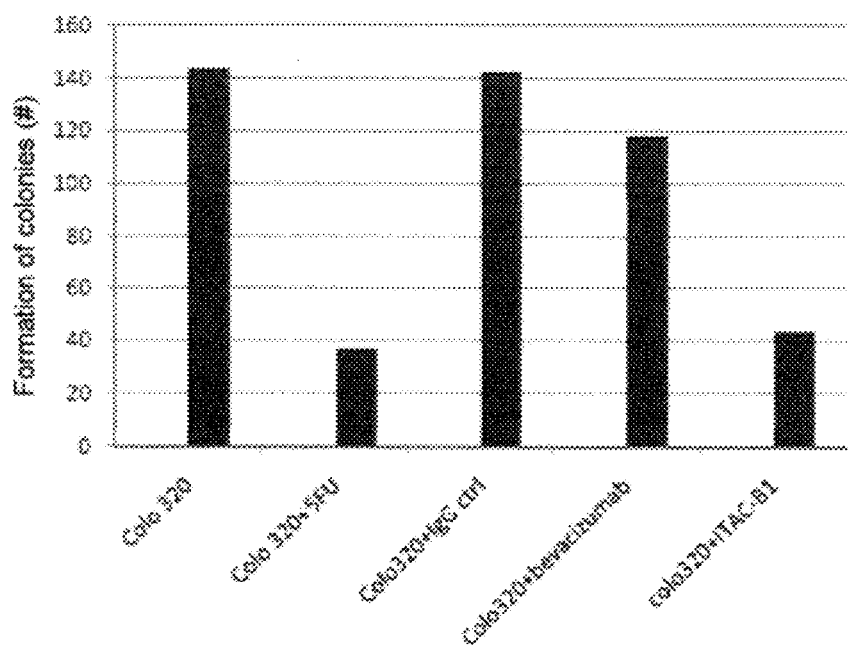
FIG. 9 illustrates a graph showing the number of tumour colonies formed (the y-axis) versus various molecules tested (the x-axis).

FIG. 9 represents the results obtained. The number of colonies formed is indicated on the y-axis, and the various molecules tested are indicated on the x-axis.

These results show that, in the presence of the ITAC-B1 antibody, as in the presence of 5-FU, the number of colonies is approximately 40, versus more than 140 for the "cells alone" control or the negative control, and approximately 120 colonies when the cells are cultured in the presence of Avastin® (bevacizumab).

It emerges from this in vitro study that the ITAC-B1 anti-NRP-2 antibodies almost completely inhibit the formation of tumour colonies of cells expressing NRP-2 at their surface, in a manner that is more efficient than with Avastin® (bevacizumab).

Since neuropilin-2 is a coreceptor for VEGF, it was verified whether the activity of ITAC-B1 was dependent on an interaction between NRP-2 and the VEGF produced by the Colo320 cells. With this aim, the tests for Colo320-cell colony formation were carried out under the conditions described above, and in the presence of ITAC-B1 antibody (10 µg/ml), of bevacizumab (50 µg/ml) or of control antibody (10 µg/ml), used separately or in combination.

Figure 10:
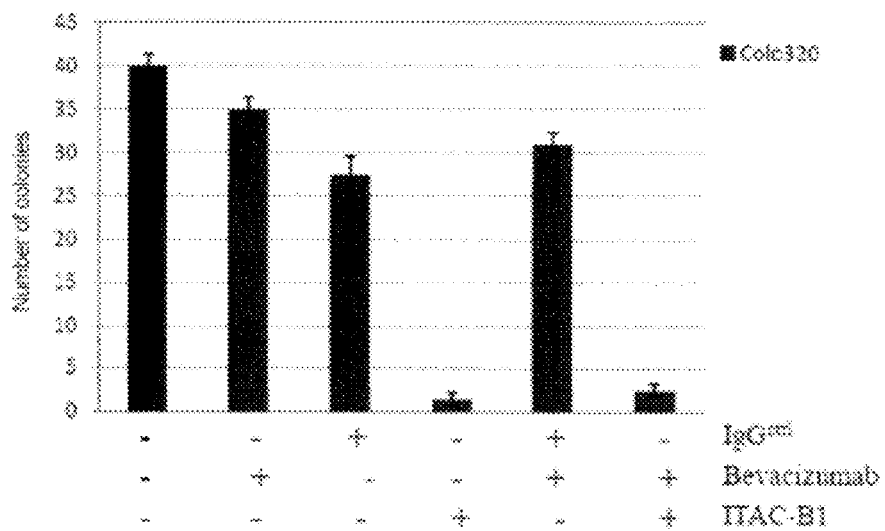
FIG. 10 illustrates a graph showing the number of Colo320 tumour colonies formed (the y-axis) versus antibodies present in the culture medium (the x-axis).

The results are given in FIG. 10: the y-axis represents the number of colonies formed; on the x-axis, the antibodies present in the culture medium are indicated by a "+".

FIG. 10 shows that the presence of bevacizumab in the culture medium has very little effect on the proliferation of the Colo320 cells: the number of colonies observed in the presence of the control antibody, of bevacizumab, or of the combination of these 2 antibodies is similar, and differs only slightly from that observed with the "cells alone" control. On the other hand, the number of colonies observed in the presence of the ITAC-B1 antibody is greatly reduced compared with the "cells alone" control; in addition, when the culture medium contains the ITAC-B1 antibody and the bevacizumab (which neutralizes VEGF-A), the number of colonies is identical to that observed when the medium contains the ITAC-B1 antibody alone. This result indicates that ITAC-B1 inhibits the cell proliferation equally effectively in the presence of VEGF and in the absence of VEGF, and therefore that the therapeutic effect of ITAC-B1 is independent of the NRP-2/VEGF interaction.

MTT Assay for Tumour Cell Proliferation:

The effect of the ITAC-B1 antibody on the proliferation of human tumour cells exhibiting NRP-2 at their membrane surface was also studied using the MTT assay, as described in Example 3 above.

4000 cells per well of Colo320$^{siRNA-ctrl}$ cells (control cells transfected with an empty vector) or of Colo320$^{siRNA-NRP-2}$ cells (transfected with an siRNA targeting NRP-2), in 100 µl of DMEM medium containing 10% of inactivated FCS, were seeded into a 96-well Maxisorp plate. After adhesion of the cells, 5 µg/ml of ITAC-B anti-NRP-2 antibody or 5 µg/ml of control antibody were added. After culture for 24, 48 or 72 hours, 10 p. 1 of MTT reconstituted at 5 mg/ml in PBS were added to each culture well. The plates were then incubated for 3 hours in the dark, at 37° C. and 5% $CO_2$, and centrifuged, and then the supernatant was removed. 200 p. 1 of DMSO were then added to each well. The optical density was read within an hour, at 570 nm, after shaking with the plate. The assay was carried out in triplicate. The results are given in FIG. 11.

Figure 11:
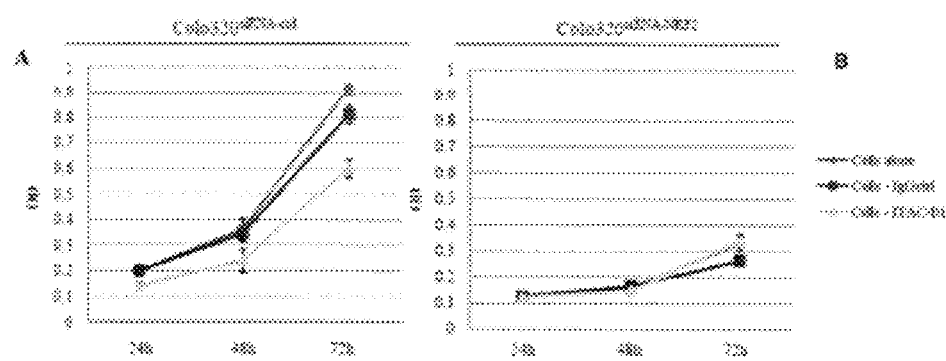
FIG. 11 represents, respectively, the results of a proliferation assay carried out with Colo320$^{siRNA-ctrl}$ cells (panel A) or Colo320$^{siRNA-NRP-2}$ cells (panel B) cells, where the optical density "OD" reflecting the production of formazan by the cells is indicated on the y-axis, and the culture time is indicated on the x-axis.

Panels A and B of FIG. 11 represent, respectively, the results obtained in the proliferation assay carried out with the Colo320$^{siRNA-ctrl}$ or Colo320$^{siRNA-NRP-2}$ cells. The optical density "OD" reflecting the production of formazan by the cells is indicated on the y-axis, and the culture time is indicated on the x-axis. The "cells alone" control is represented by ◊, the cells cultured in the presence of the control antibody are represented by ■, and the cells cultured in the presence of the ITAC-B1 antibody are represented by Δ.

These results shows that, in the case of the Colo320$^{siRNA-ctrl}$ cells which express NRP-2, the proliferation in the presence of the ITAC-B1 antibody is less than that of the cells alone and that observed in the presence of the control antibody. On the other hand, in the case of the Colo320$^{siRNA-NRP-2}$ cells, the proliferation in the presence of the ITAC-B1 antibody is identical to that of the control cells and to that observed in the presence of the control antibody. The ITAC-B1 antibodies therefore specifically slow down the proliferation of the cells exhibiting NRP-2 at the surface (Colo320$^{siRNA-ctrl}$ cells) and not that of the cells not expressing NRP-2 (Colo320$^{siRNA-NRP-2}$ cells).

EXAMPLE 5

The ITAC-B1 Antibody has the Ability to Induce Apoptosis of Tumour Cells Expressing Neuropilin-2

In order to determine the ability of the ITAC-B1 antibody to induce apoptosis of tumour cells expressing NRP-2, an in vitro Annexin V-APC apoptosis test was carried out (BD Pharmingen, San Diego, Calif.). This test is based on the externalization of phosphatidylserin by apoptotic cells and on the binding of Annexin V-APC to this molecule.

1-Pro-Apoptotic Effect of ITAC-B1 Alone 1 ml of DMEM medium containing 10% of inactivated FCS and 100 000 HT29-NRP-2 cells or 100 000 HT29ctrl cells were seeded, per well, into a 24-well Nunc plate. After adhesion of the cells (3 hours), three concentrations of ITAC-B anti-NRP-2 antibody (0.5 µg/ml, 1 µg/ml and 5 µg/ml) were tested in various wells. In parallel, "cells alone" controls were carried out, as were negative controls (anti-human mouse IgG1 antibody (BZ1) at the same concentrations as the ITAC-B1 antibody).

After incubation for 16 hours, the culture supernatant was drawn off and 500 µl of trypsin-EDTA were added to each well and left in contact for 10 minutes. When the cells began to detach, 500 µl of DMEM medium-10% FCS were added per well. The cells were then centrifuged, washed twice in PBS, and then taken up in 300 µl of 1× binding buffer (provided in the kit), and then 5 µl of Annexin V-APC were subsequently added to 100 µl of this solution. The flow cytometry analysis of the populations of cells labelled with the Annexin V-APC as a function of the concentrations of ITAC-B1 antibody, and of control antibody, is given in FIG. 12.

Figure 12:
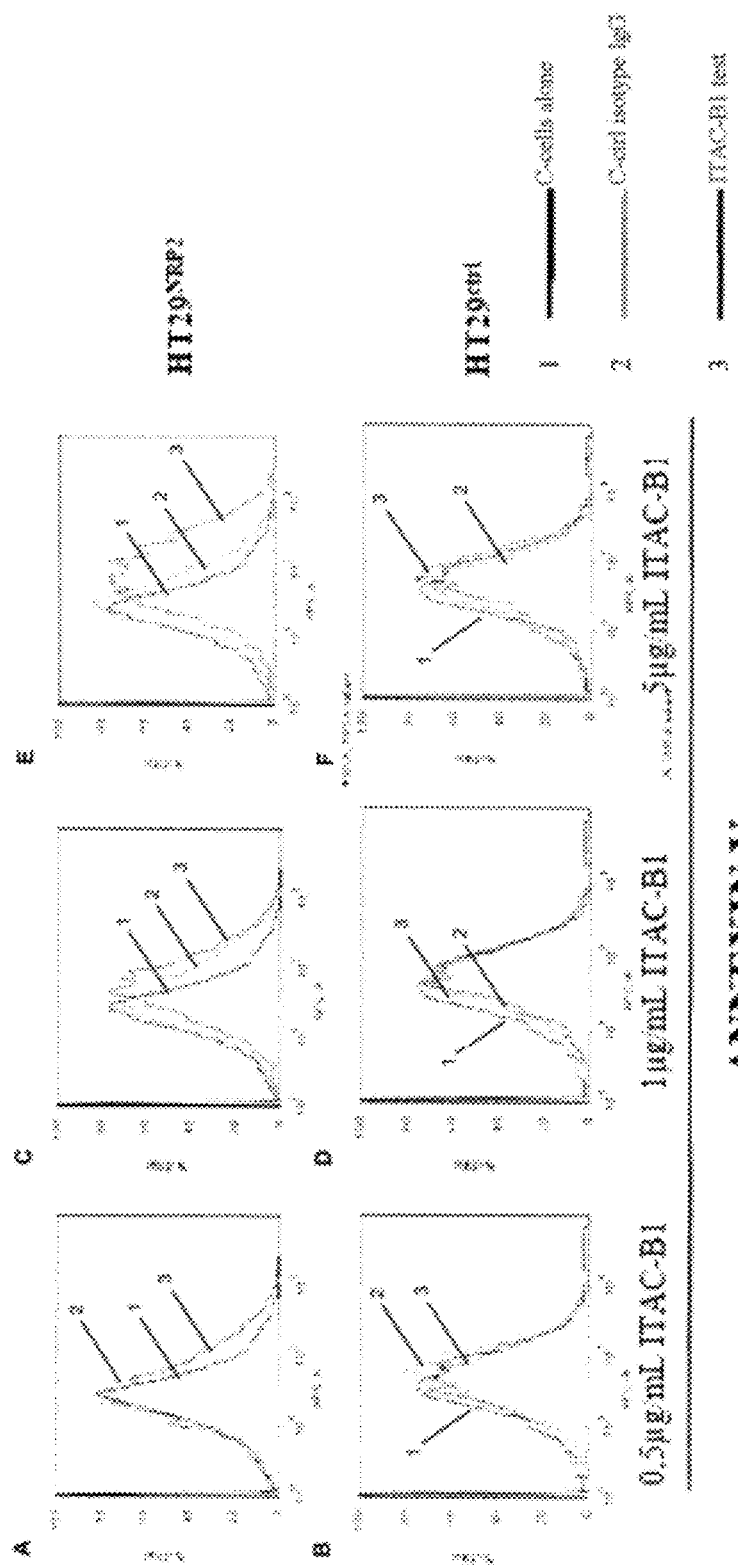
FIG. 12 represents the results obtained from flow cytometry analysis of the populations of cells labelled with Annexin V-APC as a function of the concentrations of ITAC-B1 antibody and of control antibody. Panels A, C and E represent the experiments carried out with HT29-NRP-2 cells, while panels B, D and F represent the experiments carried out with HT29ctrl cells.

For each of the panels of FIG. 12, the number of events (number of cells) is indicated on the y-axis and the fluorescence intensity (corresponding to the labelling of the cells with the Annexin V-APC) is represented on the x-axis. Panels A, C and E represent the experiments carried out with the HT29-NRP-2 cells, panels B, D and F represent the experiments carried out with the HT29ctrl cells. The experiments for which the concentration of ITAC-B1 antibody is 0.5 µg/ml are represented in panels A and B of FIG. 12. The experiments for which the concentration of ITAC-B1 antibody is 1 µg/ml are represented in panels C and D of FIG. 12, and the experiments for which the concentration of ITAC-B1 antibody is 5 µg/ml are represented in panels E and F of FIG. 12. For each panel, the distribution curve (1) represents the cells alone, the distribution curve (2) represents the cells cultured in the presence of a control murine isotype antibody and the distribution curve (3) represents the cells cultured in the presence of the ITAC-B1 antibody.

For panels C and E representing the experiments carried out with the HT29-NRP-2 cells expressing NRP-2, a shift towards the right is observed for the distribution peak corresponding, respectively, to the concentrations of 1 and 5 µg/ml of ITAC-B1 antibody. This shift in the distribution peak is not observed for the "cells alone" and "control antibody" controls. This result indicates that apoptosis is specifically induced in the cells expressing NRP-2 starting from 1 µg/ml of ITAC-B1 antibody in the culture medium.

As regards the corresponding experiments carried out with the HT29ctrl cells which do not express NRP-2, curves representing the conditions: cells alone, and control-antibody and ITAC-B1-antibody controls, are superimposed, indicating that the ITAC-B1 antibody does not bring about the apoptosis of cells not expressing NRP-2.

It is noted that the ITAC-B1 antibody induces apoptosis of cells expressing NRP-2 at their cell surface, at a dose greater than or equal to 1 µg/ml. The apoptosis induced by ITAC-B1 is dose-dependent since a higher concentration of ITAC-B1 leads to greater apoptosis.

These experiments therefore show that the ITAC-B1 antibody specifically induces apoptosis of tumour cells exhibiting NRP-2 (HT29-NRP-2) at their membrane surface, without inducing apoptosis of cells not exhibiting NRP-2 (HT29).

II—Pro-Apoptotic Effect of ITAC-B1 in Combination with Other Anticancer Agents

Similar experiments for evaluating the ability of ITAC-B1 to induce apoptosis of cells expressing NRP-2 were carried out with cells culturing the presence either of 5-FU (5-fluorouracil) or of irinotecan, two anticancer agents commonly used in chemotherapy. In this series of experiments, the ITAC-B1-antibody concentrations of 2.5 µg/ml and 5 µg/ml were tested. In parallel, "cells alone" controls were carried out, as were controls with the BZ1 antibody at the concentrations of 2.5 µg/ml and 5 µg/ml. The 5-FU and the irinotecan were used at 10 µg/ml. The results of these experiments are represented in FIG. 13.

Figure 13:
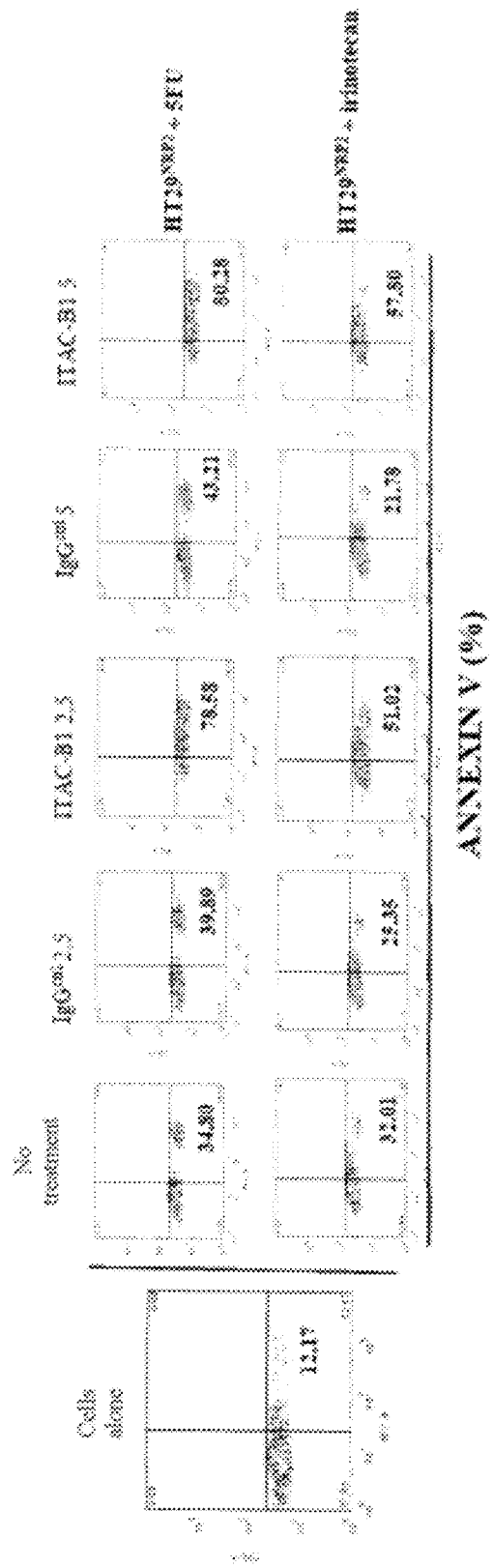
FIG. 13 illustrates point-cloud representations of the flow cytometry analysis of experiments for evaluating the ability of ITAC-B1 to induce apoptosis of cells expressing NRP-2 with cells culturing the presence either of 5-FU (5-fluorouracil) or of irinotecan.

The panels of FIG. 13 are point-cloud representations of the flow cytometry analysis. For each of the panels, the fluorescence intensity (corresponding to the labelling of the cells with Annexin V-APC) is represented on the x-axis. The y-axis indicates the granulosity of the cells (Side Scatter or SSC). The antibody-treatment conditions are indicated above the panels, and the treatment with 5-FU or irinotecan is indicated to the right of the panels. The percentage of cells labelled with Annexin V-APC (corresponding to the percentage of cells having entered into apoptosis) is indicated at the bottom-right of each panel.

The cells alone exhibit approximately 12% apoptosis, and the cells cultured in the presence of 5-FU or irinotecan alone, or combined with the BZ1 control antibody, exhibit between approximately 34% and 43% apoptosis in the case of 5-FU, and between 21% and 35% apoptosis in the case of irinotecan.

The apoptosis in the cells cultured jointly in the presence of 5-FU and of the ITAC-B1 antibody is of the order of 78.5% for an ITAC-B1 concentration in the medium of 2.5 µg/ml, and of the order of 80% for an ITAC-B1 concentration of 5 µg/ml.

For the cells cultured in the presence of irinotecan and of ITAC-B1, the apoptosis is of the order of 51% for an ITAC-B1 antibody concentration of 2.5 µg/ml, and of the order of 58% for a concentration of 5 µg/ml.

These results therefore demonstrate a synergy of action between the ITAC-B1 antibodies and the anticancer molecules, the 5-FU/ITAC-B1 combination being the most effective under the conditions tested.

III—The Pro-Apoptotic Effect of ITAC-B1 is Correlated with p53 Expression

In order to correlate the induction of apoptosis with p53 expression, the Colo320siRNA-ctrl cells were pretreated for 18 h with a chemical inhibitor of p53, pifithrin-α, at a dose of 27 µM (PFTα, Sigma). After pretreatment, the cells are washed twice with 3 ml of PBS and placed in a 24-well plate, at a rate of 100 000 cells/well in 1 ml of RPMI-10% FCS. Non-pretreated cells are placed under the same conditions. The cells are incubated for 5 h with a control murine isotype antibody (BZ1) or ITAC-B1 at 20 µg/ml and the apoptosis is measured as described above.

Figure 14:
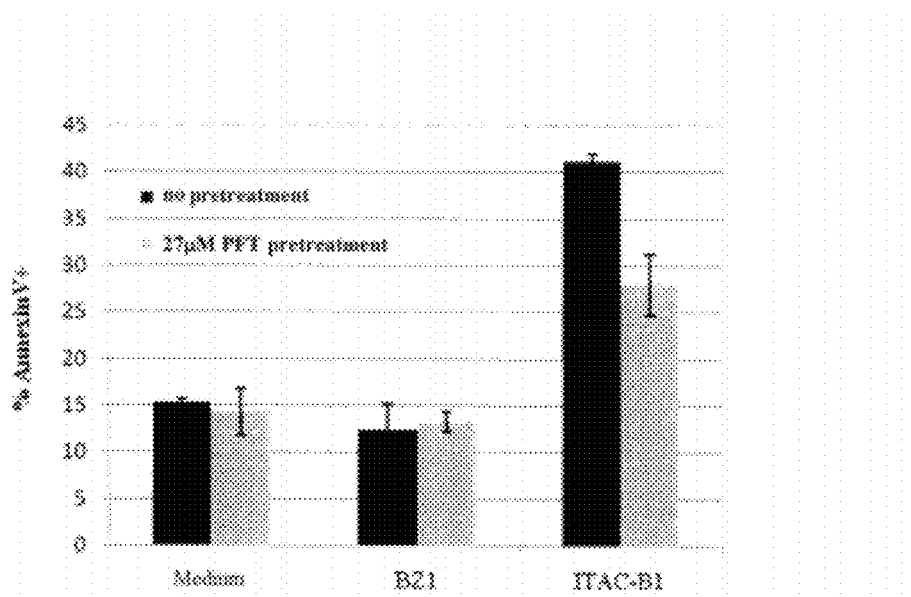
FIG. 14 represents the results of the apoptosis-induction experiments carried out with Colo320$^{siRNA-ctrl}$ cells pretreated or not pretreated with PFTα.

FIG. 14 represents the results of the apoptosis-induction experiments carried out with the Colo320siRNA-ctrl cells pretreated or not pretreated with PFTα. The percentage of cells labelled with Annexin V-APC is indicated on the y-axis, the cell culture conditions are indicated on the x-axis (control consisting of medium, control consisting of medium supplemented with a control isotype antibody -BZ1-, test consisting of medium supplemented with the ITAC-B1 antibody). The results of the tests carried out with cells pretreated with PFTα are represented in light grey, those of the tests carried out with non-pretreated cells are represented in dark grey.

While, in the control consisting of medium and the control consisting of medium supplemented with control antibody the labelling with Annexin V-APC is similar whether or not the cells are treated with PFTα, it is noted that the cells cultured in the presence of ITAC-B1 antibody are more weakly labelled when they are pretreated with PFTα (approximately 28% labelling versus 41% for the non-pretreated cells).

These results show that the pretreatment with PFTα prevents the ITAC-B1-dependent apoptosis. The ITAC-B1-induced apoptosis therefore appears to be dependent on p53 expression.

IV—The Pro-Apoptotic Effect of ITAC-B1 is VEGF-Independent

In order to determine whether the apoptotic effect observed during the treatment of the cells with the ITAC-B1 antibody was dependant on the binding of VEGF to NRP-2, the HT29-NRP-2 cells expressing NRP-2 (and which, like the Colo320 cells, naturally secrete VEGF into the culture medium) were cultured in the presence of the anti-VEGF humanized monoclonal antibody Avastin® (bevacizumab) at 50 µg/ml, and the cells were then incubated in the presence of a control murine isotype antibody (BZ1) or of ITAC-B1 at 20 µg/ml for 6 hours. The apoptosis induced was then measured by labelling with Annexin V-APC as described above. The results are given in FIG. 15.

Figure 15:
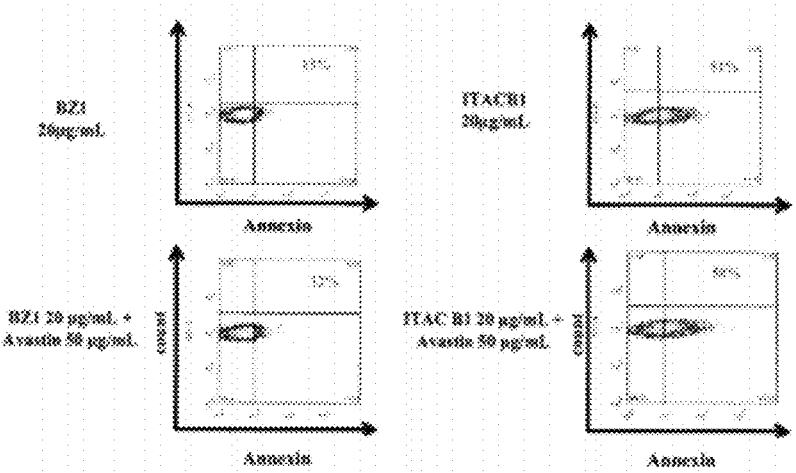
FIG. 15 illustrates the point-cloud representations of the flow cytometry analysis of HT29-NRP-2 cells expressing NRP-2 which were cultured in the presence of Avastin® followed by incubation of the cells in the presence of BZ1 or of ITAC-B1.

The panels of FIG. 15 are point-cloud representations of the flow cytometry analysis. For each of the panels, the fluorescence intensity (corresponding to the labelling of the cells with Annexin V-APC) is represented on the x-axis. The y-axis indicates the granulosity (side scatter) of the cells. The conditions of treatment with the antibodies and the Avastin® are indicated to the left of the panels. The percentage of cells labelled with the Annexin V-APC, corresponding to the percentage of cells having entered into apoptosis, is indicated at the top-right of each panel.

The cells cultured in the presence of the BZ1 control antibody, with or without Avastin®, exhibit respectively 12% and 13% apoptosis. The apoptosis in the HT29-NRP-2 cells cultured in the presence of the ITAC-B1 antibody is of the order of 51%, and approximately 58% of the cells were pretreated with Avastin®.

These results clearly show that the neutralization of the VEGF does not impair the ability of the ITAC-B1 antibody to induce apoptosis, thereby confirming that the pro-apoptotic properties of the ITAC-B1 antibody are VEGF-independent.

EXAMPLE 6

ITAC-B1 does not Influence Phosphorylation of the VEGFR1 Receptor of the AKT Protein The possible effect of the ITAC-B1 antibody on the degree of phosphorylation of a VEGF receptor (VEGFR1), and also on the phosphorylation of the AKT protein which is activated by means of the VEGF receptors, was studied on HT29-NRP-2 and Colo320$^{siRNA-ctrl}$ tumour cells.

Figure 16:
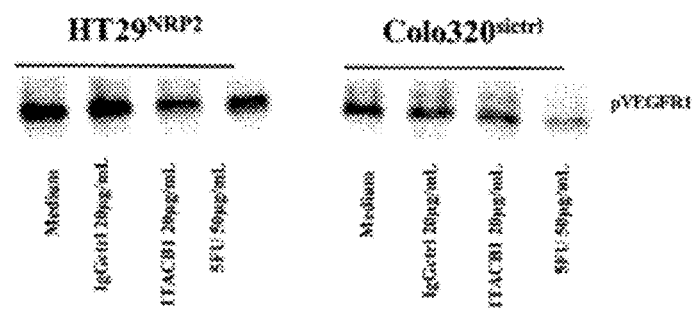
FIGS. 16 and 17 show that the phosphorylation status of VEGFR and also the amount of AKT and its phosphorylation status are similar, irrespective of whether or not the cells are treated with ITAC-B1, demonstrating that the effects of this antibody are not linked to the VEGF/VEGFR signalling pathway.
Figure 17:
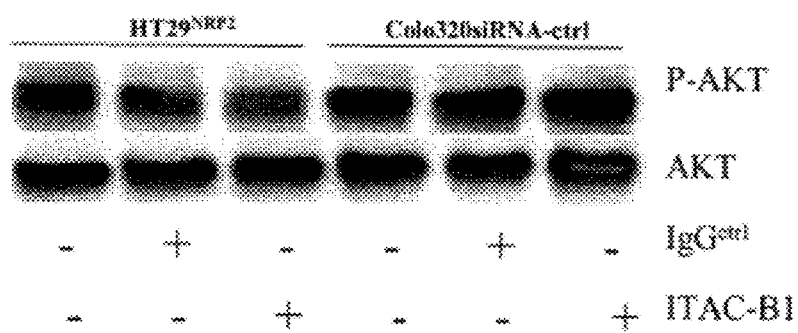

The cells were cultured for 24 hours in RPMI medium+10% FCS in the presence of the BZ1 control antibody at 20 µg/ml, of ITAC-B1 at 20 µg/ml or of 5-FU at 50 µg/ml. A "nontreated cell" control was added ("medium" control). The cells were then isolated and lysed, and the phosphorylation of VEGFR-1 and of AKT was evaluated by Western blotting on the cell protein extracts, using antibodies directed against nonphosphorylated VEGFR1 (anti-VEGFR1 rabbit polyclonal antibody) or phosphorylated VEGFR1 (anti-phospho-VEGFR1$^{Tyr1213}$ rabbit polyclonal antibody, R&D systems) or antibodies directed against nonphosphorylated AKT (rabbit polyclonal antibody C67E7, Cell Signaling technology) or phosphorylated AKT (anti-phospho-AKT$^{Ser473}$ rabbit polyclonal antibody DE-9, Cell Signaling technology). The results are represented in FIGS. 16 and 17.

These results show that the phosphorylation status of VEGFR and also the amount of AKT and its phosphorylation status are similar, irrespective of whether or not the cells are treated with ITAC-B1, demonstrating that the effects of this antibody are not linked to the VEGF/VEGFR signalling pathway.

EXAMPLE 7

Search for any Interaction Between VEGF and the Neuropilin-2 Epitope Recognized by ITAC-B1

In order to demonstrate any competition between VEGFa and ITAC-B1 for the recognition of neuropilin-2, HT29-NRP-2 tumour cells expressing neuropilin-2 were preincubated with or without VEGF (1000 ng/ml) for 15 minutes. These cells were then incubated with the ITAC-B1 antibody or with a control isotype antibody (BZ1 antibody), and analysed by flow cytometry as described in Example 2 above.

Figure 18:
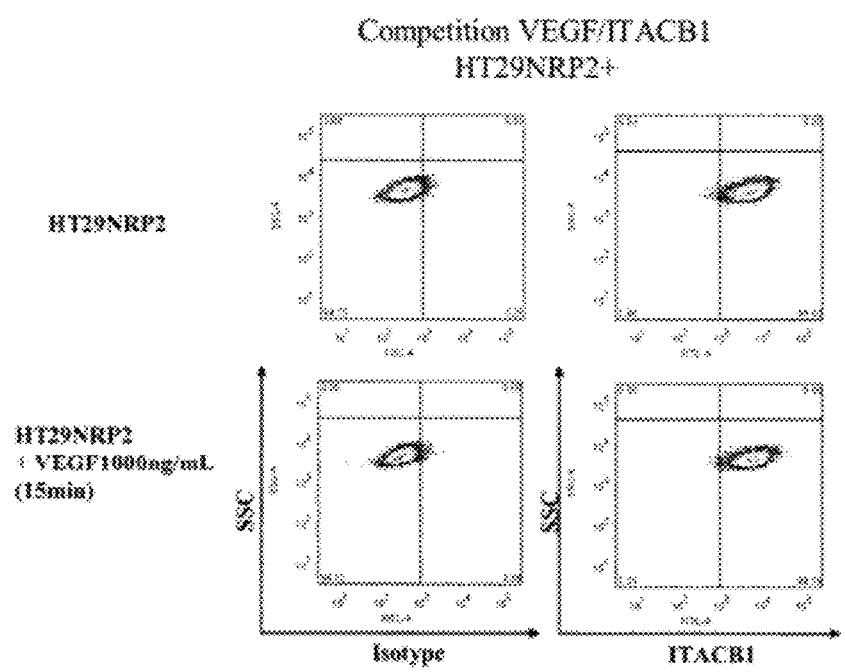
FIG. 18 shows that the presence of VEGFa does not prevent the binding of ITAC-B1 to the tumour cells.

The results are illustrated by FIG. 18. These results show that the presence of VEGFa does not prevent the binding of ITAC-B1 to the tumour cells.

EXAMPLE 8

The ITAC-B1 and ITAC-B2 Antibodies have the Ability to Induce Expression of the p53 Protein After having shown that neuropilin-2 has the ability to alter the expression of p53 in the HT29 line and to restore it in the Colo320$^{siRNA-NRP-2}$ line, the influence of the ITAC-B1 antibody on the expression of p53 in the lines expressing neuropilin-2, such as HT29-NRP-2 and Colo320$^{siRNA-ctrl}$ was studied.

Figure 19:
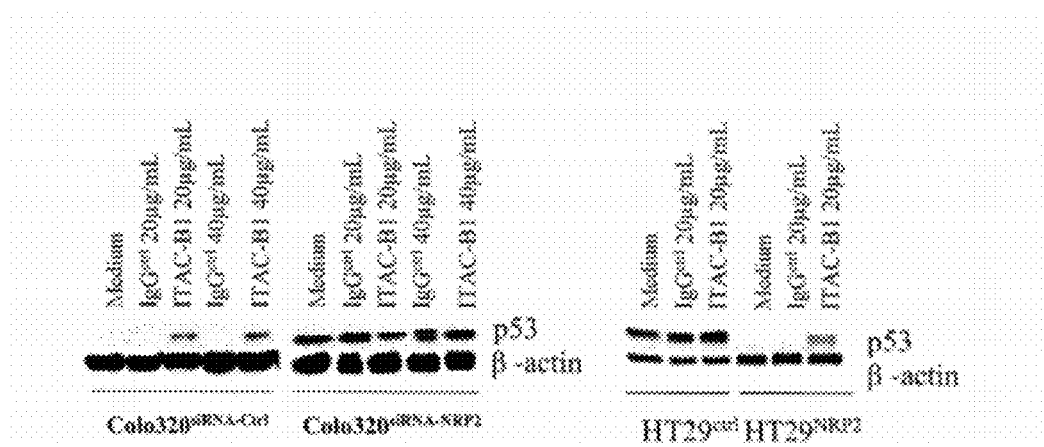
FIG. 19 shows that the p53 protein is strongly expressed in the HT29-ctrl and Colo320$^{siRNA-NRP-2}$ lines which do not express NRP-2, irrespective of whether or not the ITAC-B1 antibody is present in the medium.

The HT29, HT29-NRP-2, Colo320$^{siRNA-ctrl}$ tumour cells and Colo320$^{siRNA-NRP-2}$ were exposed to 20 ng/ml of ITAC-B1 antibody or of control antibody, and cultured for 48 hours. After lysis of the cell lines, migration of the protein pellets obtained on a 10% polyacrylamide gel (10 µg of protein per well) and then transfer onto a PVDF membrane, the membrane was incubated overnight with the anti-p53 primary antibody (BD Biosciences, mouse anti-human p53) diluted to 1/500. After washing in TBS/0.1% Tween20, the membranes were incubated for 1 hour with an anti-mouse IgG-HRP secondary antibody diluted to 1/6000. The results are represented in FIG. 19.

These results show that the p53 protein is strongly expressed in the HT29-ctrl and Colo320$^{siRNA-NRP-2}$ lines which do not express NRP-2, irrespective of whether or not the ITAC-B1 antibody is present in the medium. When the HT29-NRP-2 and Colo320$^{siRNA-ctrl}$ lines which express NRP-2 are cultured alone or in the presence of the control antibody, p53 is not detected, while the presence of the ITAC-B1 antibody in the culture medium partly restores the expression of p53. These results therefore show that the treatment of cells expressing NRP-2 at their membrane surface (HT29-NRP-2 and Colo320$^{siRNA-ctrl}$) with ITAC-B1 results in restoration of the expression of p53 in the tumour lines.

This experiment confirms that a negative correlation exists between the presence of neuropilin-2 and of p53, and that ITAC-B1 has the original capacity of being able to modulate the level of p53 expression.

EXAMPLE 7

Use of the ITAC-B1 Antibody to Potentiate the Effect of Anti-Neoplastic Treatments In Vivo HT29-NRP-2 tumour cells were injected subcutaneously into 20 immunodeficient mice, at a rate of 1×10⁶ cells per mouse, in the right flank. 10 days after the injection, the tumours measure approximately 5 mm×5 mm. Four groups of 3 mice having comparable tumours were formed: each group received, intraperitoneally, either PBS (control group A), or the ITAC-B1 antibody (group B), or 5-FU (group C), or 5-FU and the ITAC-B1 antibody (group D).

Figure 20:
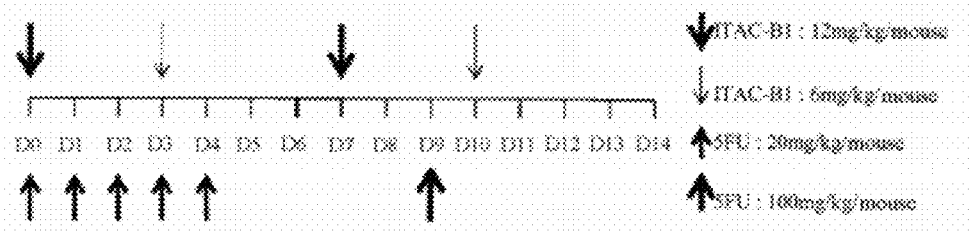
FIG. 20 is a schematic representation of a chemotherapy treatment protocol.

The chemotherapy treatment protocol is represented schematically in FIG. 20.

In accordance with the protocol described above, group B was inoculated with ITAC-B1 at D0 (12 mg/kg), D3 (6 mg/kg), D7 (12 mg/kg) and D10 (6 mg/kg). Group C was inoculated with 20 mg/kg of 5-FU from D0 to D4 and then with 100 mg/kg at D9. Group D was inoculated with ITAC-B1 at D0 (12 mg/kg), D3 (6 mg/kg), D7 (12 mg/kg) and D10 (6 mg/kg) and with 20 mg/kg of 5-FU from D0 to D4 and 100 mg/kg of 5-FU at D9.

The tumours were measured twice a week, and the volume of the tumours was calculated with the formula: $V (mm^3) = d^2 \times D/2$. The results of these measurements are shown in FIG. 21.

Figure 21:
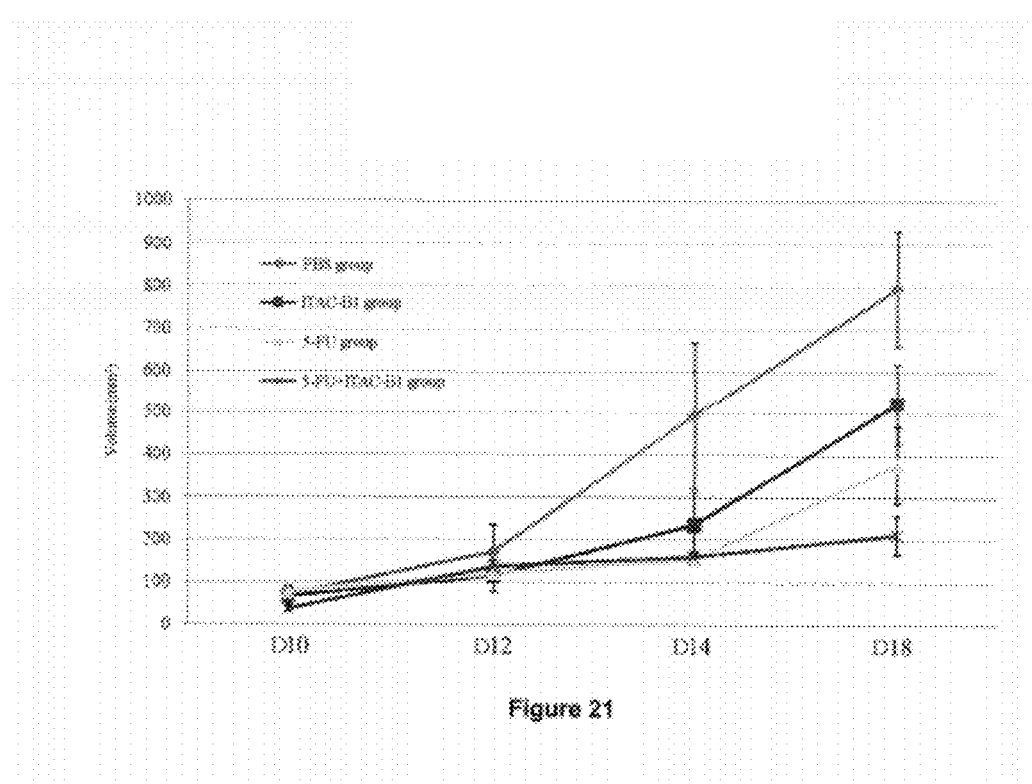
FIG. 21 represents the tumour volume as a function of time, where Group A (PBS control) is represented by (◊), group B (mice inoculated with the ITAC-B1 antibody) is represented by (■), group C (mice inoculated with 5-FU) is represented by (δ), and group D (mice inoculated both with the ITAC-B1 antibody and with 5-FU) is represented by (x).

FIG. 21 represents the tumour volume as a function of time. Group A (PBS control) is represented by (◇), group B (mice inoculated with the ITAC-B1 antibody) is represented by (■), group C (mice inoculated with 5-FU) is represented by (Δ), and group D (mice inoculated both with the ITAC-B1 antibody and with 5-FU) is represented by (x).

A reduction in tumour volume is observed starting from D14 in the mice inoculated with the ITAC-B1 antibody or with 5-FU. This reduction is more marked during the combined 5-FU/ITAC-B1 treatment.

These results show that the ITAC-B1 antibody is capable of slowing down tumour growth, in vivo. In addition, since the mice treated with 5-FU combined with ITAC-B1 experience the greatest slowing of tumour growth, compared with the mice treated with 5-FU alone or ITAC-B1 alone, these results clearly show that the use of the ITAC-B1 antibody potentiates the effectiveness of the 5-fluorouracil.

The invention claimed is:

1. An anti-human neuropilin-2 antibody, characterized in that the binding thereof to tumour cells expressing human neuropilin-2 induces apoptosis of said tumour cells wherein the antibody is chosen from the following:
   i. an antibody comprising the variable domain of the heavy chain and the variable domain of the light chain of the ITAC-B1 antibody, said domains being respectively defined by the sequences SEQ ID NO: 2 and SEQ ID NO: 4;
   ii. an antibody comprising the variable domain of the heavy chain and the variable domain of the light chain of the ITAC-B2 antibody, said domains being respectively defined by the sequences SEQ ID NO: 6 and SEQ ID NO: 8.

2. A polypeptide which binds to human neuropilin2 derived from an antibody as in claim 1, characterized in that it comprises at least the CDR1, CDR2 and CDR3 of the heavy chain and the CDR1, CDR2 and CDR3 of the light chain of the ITAC-B1 antibody, wherein said CDRs are respectively defined by sequences SEQ ID NO: 9 to 14, or of the ITAC-B2 antibody, wherein said CDRs are respectively defined by sequences SEQ ID NO: 15 to 20.

3. The polypeptide according to claim 2, characterized in that it is a humanized antibody.

4. A method of treating a tumor containing tumor cells which express human neuropilin-2 in a subject in of such treatment comprising administering an amount of the antibody of claim 1 effective to bind to human neuropilin-2 on the tumor cell.

5. The method of claim 4 wherein the amount of the antibody is effective to increase p53 expression in the tumor cell upon binding to human neuropilin-2.

6. The method of claim 4 wherein the amount of antibody is effective to induce apoptosis of the tumor cell upon binding to human neuropilin-2.

7. A method of treating a tumor containing tumor cells which express human neuropilin-2 in a subject in of such treatment comprising administering an amount of the polypeptide of claim 3 effective to bind to human neuropilin-2 on the tumor cell.

8. The method of claim 7 wherein the amount of the polypeptide is effective to increase p53 expression in the tumor cell upon binding to human neuropilin-2.

9. The method of claim 7 wherein the amount of polypeptide is effective to induce apoptosis of the tumor cell upon binding to human neuropilin-2.

* * * * *